United States Patent
Tsang et al.

(10) Patent No.: US 11,096,623 B2
(45) Date of Patent: Aug. 24, 2021

(54) SYSTEMS AND METHODS FOR EVALUATION OF SCOLIOSIS AND KYPHOSIS

(71) Applicant: AVALON SPINECARE (HK) LIMITED, Central (HK)

(72) Inventors: Yuk Lun Tsang, Kowloon (HK); Lut Hey Chu, Kowloon (HK); Johnson Yiu-Nam Lau, Houston, TX (US)

(73) Assignee: Avalon Spinecare (HK) Limited, New Territories (HK)

( * ) Notice: Subject to any disclaimer, the term of this patent is extended or adjusted under 35 U.S.C. 154(b) by 263 days.

(21) Appl. No.: 16/339,630

(22) PCT Filed: Oct. 5, 2017

(86) PCT No.: PCT/US2017/055433
§ 371 (c)(1),
(2) Date: Apr. 4, 2019

(87) PCT Pub. No.: WO2018/067883
PCT Pub. Date: Apr. 12, 2018

(65) Prior Publication Data
US 2019/0239797 A1    Aug. 8, 2019

Related U.S. Application Data

(60) Provisional application No. 62/404,578, filed on Oct. 5, 2016, provisional application No. 62/514,599, filed on Jun. 2, 2017.

(51) Int. Cl.
| | |
|---|---|
| *A61B 5/00* | (2006.01) |
| *A61B 5/107* | (2006.01) |
| *A61B 5/11* | (2006.01) |
| *A61B 90/00* | (2016.01) |

(Continued)

(52) U.S. Cl.
CPC .......... *A61B 5/4561* (2013.01); *A61B 5/0002* (2013.01); *A61B 5/0064* (2013.01);
(Continued)

(58) Field of Classification Search
CPC ................ A61B 5/4561; A61B 5/6823; A61B 5/4566; A61B 5/0064; A61B 5/1071
See application file for complete search history.

(56) References Cited

U.S. PATENT DOCUMENTS

| | | | | |
|---|---|---|---|---|
| 3,955,285 A | * | 5/1976 | Moeckl ................ | A61B 5/1077 33/515 |
| 4,762,134 A | * | 8/1988 | Gala .................... | A61B 5/1104 600/594 |

(Continued)

FOREIGN PATENT DOCUMENTS

| | | |
|---|---|---|
| KR | 1020100052672 | 5/2010 |
| KR | 1020150059244 | 6/2015 |

OTHER PUBLICATIONS

PCT Search Report & Written Opinion dated Jan. 30, 2018 for PCT/US2017/055433 in the name of Avalon Spinecare (HK) Limited filed on Oct. 5, 2017 (16 pages).

*Primary Examiner* — Sean P Dougherty
(74) *Attorney, Agent, or Firm* — Fish IP Law, LLP

(57) ABSTRACT

Devices, systems, and methods for characterizing a condition of spinal deformities are contemplated. Mobile devices that incorporate inclinometers or accelerometers are held securely in a supporting structure. Supporting structures can include features that secure the mobile device in an upper portion and a lower portion that includes at least one roller, and a centrally placed notch dimensioned to permit the assembled device to span the width of a typical human spinal column. The roller includes an encoder that provides a measure of distance travelled as the device rolls. The support device can include additional features, such as additional (Continued)

sensors that are accessible by the mobile device, a centrally placed guide that can be used to keep the assembled device in alignment during use, and supplementary battery power for the mobile device.

7 Claims, 20 Drawing Sheets

(52) U.S. Cl.
CPC .............. *A61B 5/1071* (2013.01); *A61B 5/11* (2013.01); *A61B 5/4566* (2013.01); *A61B 5/6823* (2013.01); *A61B 5/6897* (2013.01); *A61B 5/6898* (2013.01); *A61B 5/742* (2013.01); *A61B 5/0053* (2013.01); *A61B 5/4836* (2013.01); *A61B 2090/064* (2016.02); *A61B 2560/0223* (2013.01); *A61B 2560/0425* (2013.01); *A61B 2562/0219* (2013.01); *A61B 2562/0252* (2013.01); *A61B 2562/046* (2013.01)

(56) References Cited

U.S. PATENT DOCUMENTS

| | | | | |
|---|---|---|---|---|
| 4,875,470 | A * | 10/1989 | Cotone | A61H 15/0078 601/117 |
| 5,088,475 | A * | 2/1992 | Steffensmeier | A61H 15/0078 601/102 |
| 5,101,835 | A * | 4/1992 | DelRe | A61B 5/1077 33/512 |
| 5,181,525 | A * | 1/1993 | Bunnell | A61B 5/1077 600/594 |
| 5,441,413 | A * | 8/1995 | Kumar | G09B 23/28 434/262 |
| 6,190,338 | B1 * | 2/2001 | Arndt | A61H 1/00 601/102 |
| 6,258,047 | B1 * | 7/2001 | Muramatsu | A61B 5/103 600/594 |
| 6,351,549 | B1 * | 2/2002 | Souluer | A61B 5/0053 382/131 |
| 6,500,131 | B2 * | 12/2002 | Leitner | A61B 5/064 600/409 |
| 6,539,328 | B1 * | 3/2003 | Cremonese | A61B 5/103 702/151 |
| 6,637,278 | B1 * | 10/2003 | Fasanella | A61B 5/103 33/512 |
| 2002/0049393 | A1 * | 4/2002 | Cook | A61B 5/103 600/594 |
| 2005/0148839 | A1 * | 7/2005 | Shechtman | A61B 5/4561 600/407 |
| 2006/0015042 | A1 | 1/2006 | Linial et al. | |
| 2007/0149899 | A1 | 6/2007 | Shechtman et al. | |
| 2011/0237990 | A1 * | 9/2011 | Marsten | A61H 15/00 601/119 |
| 2014/0188008 | A1 | 7/2014 | Ragnarsdottir et al. | |
| 2017/0347919 | A1 * | 12/2017 | Bollman | A61B 5/1075 |

* cited by examiner

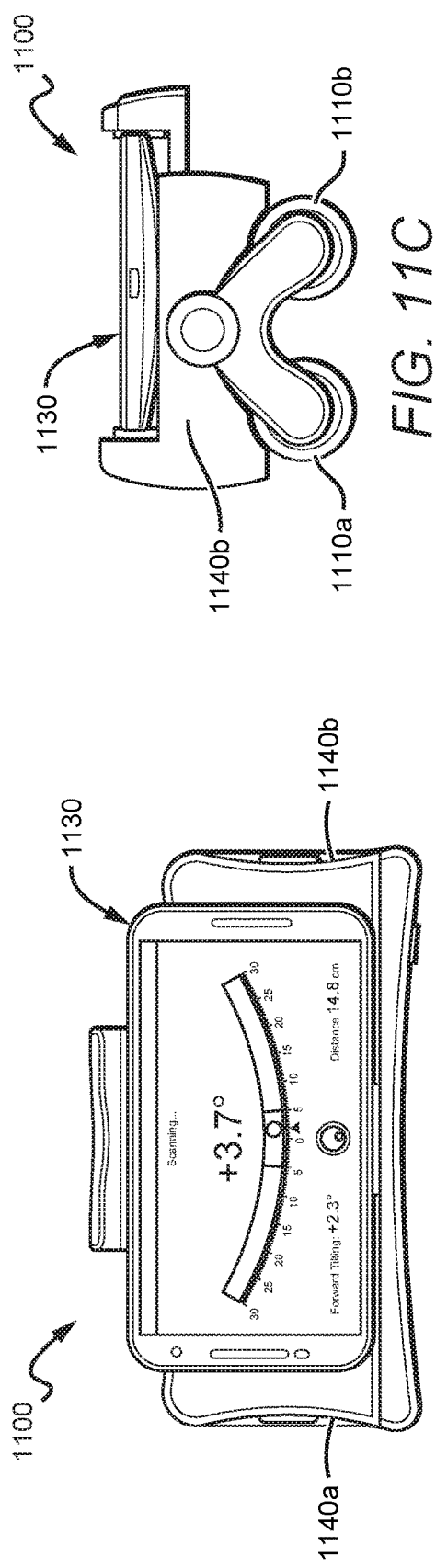
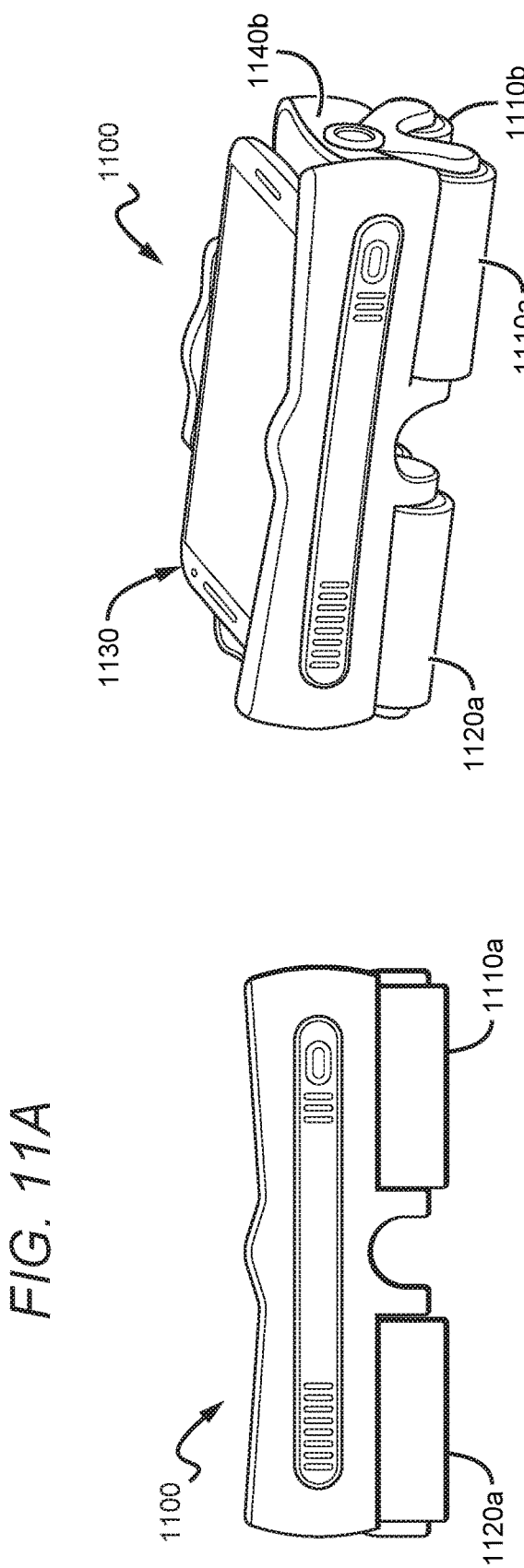

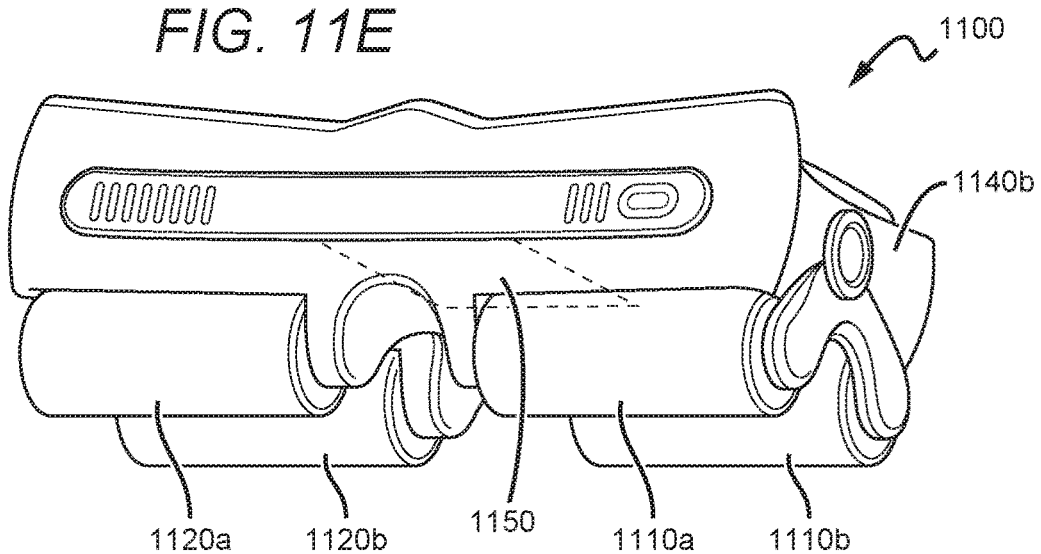
FIG. 11E
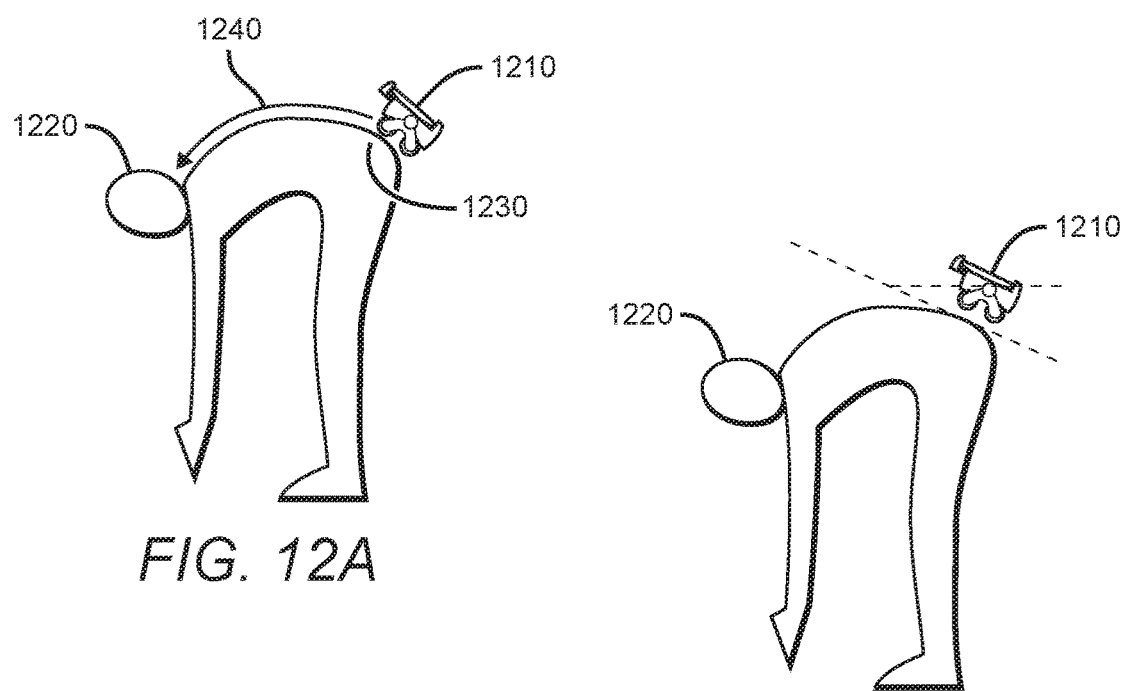
FIG. 12A
FIG. 12C
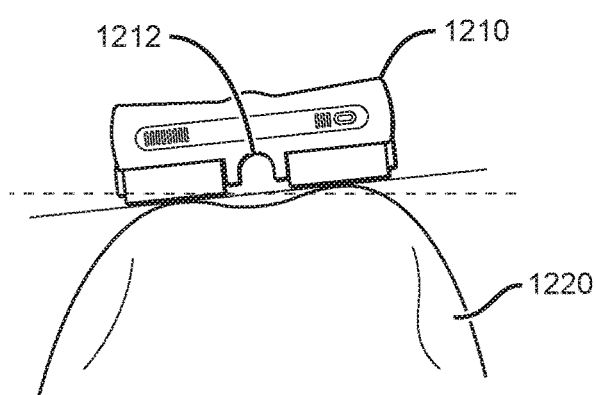
FIG. 12B

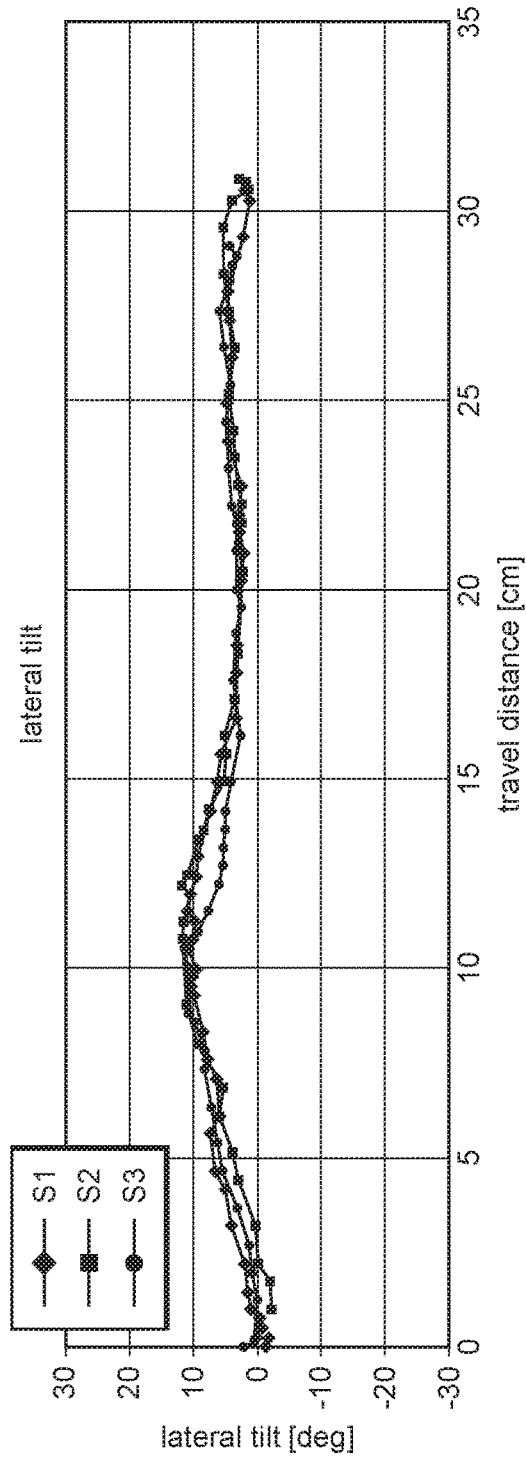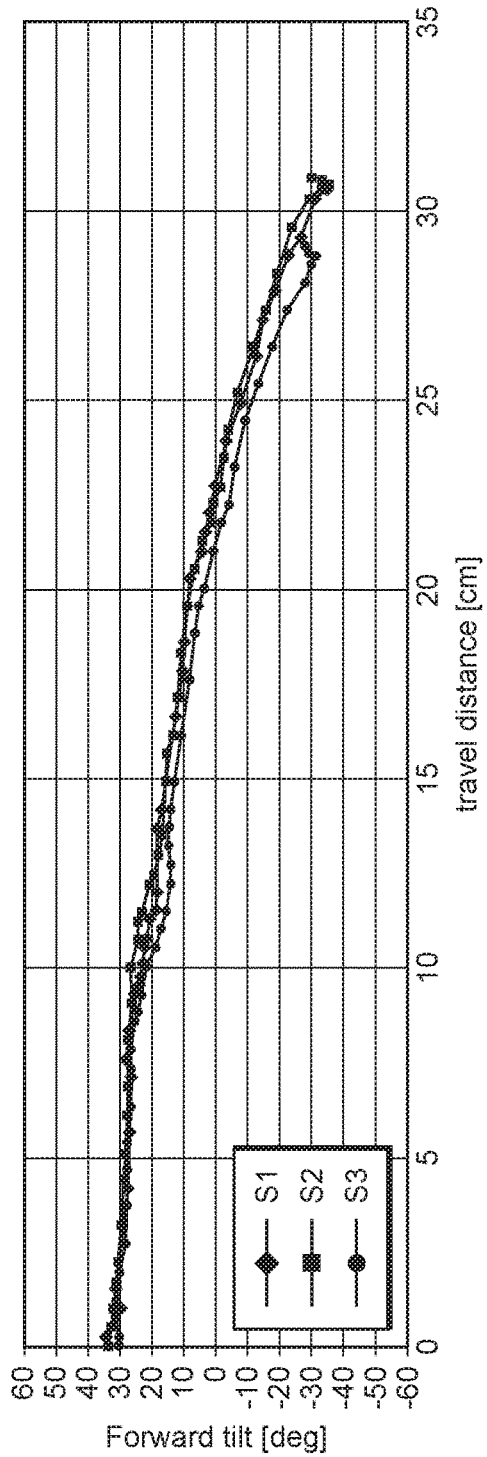

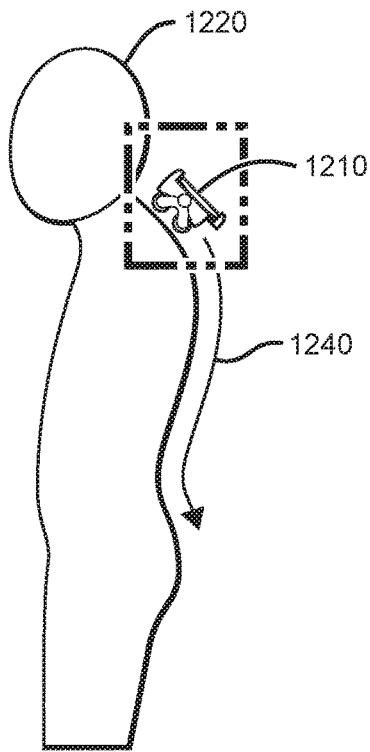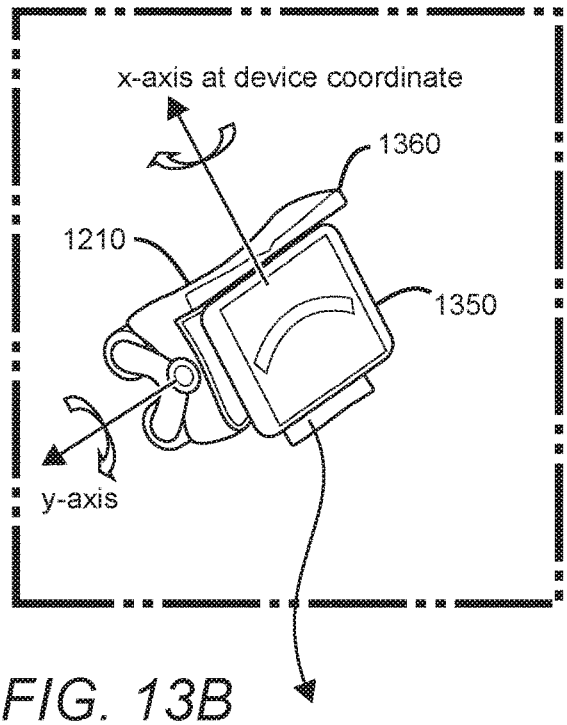
FIG. 13A
FIG. 13B
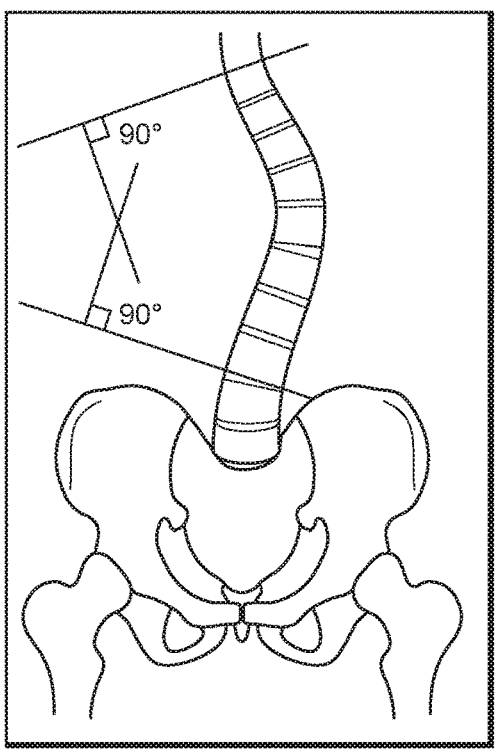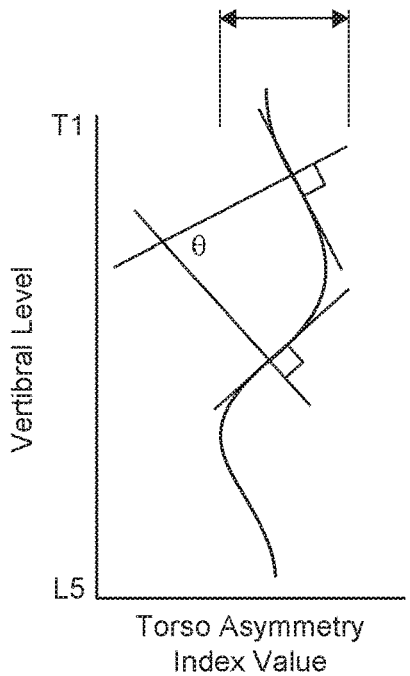
FIG. 14A
PRIOR ART
FIG. 14B
PRIOR ART

SYSTEMS AND METHODS FOR EVALUATION OF SCOLIOSIS AND KYPHOSIS

This application claims priority to U.S. provisional application having Ser. No. 62/404,578, filed Oct. 5, 2016, and U.S. provisional application having Ser. No. 62/514,599, filed Jun. 2, 2017.

FIELD OF THE INVENTION

The field of the invention is diagnostic devices and methods for use in orthopedics, particularly for conditions related to the spine.

BACKGROUND

The background description includes information that may be useful in understanding the present invention. It is not an admission that any of the information provided herein is prior art or relevant to the presently claimed invention, or that any publication specifically or implicitly referenced is prior art.

Scoliosis is a deformity of the spine in which portions of the spinal column are displaced laterally. Similarly, kyphosis is a deformity of the spine in which portions of the spinal column are displaced anteriorly and dorsally to produce a curved or "humped" back. These deformities have a variety of causes and can appear at any stage of life. If such deformities reach dangerous magnitudes or are progressing, surgical intervention can be used to halt progression and correct or reduce the deformity. Alternatively, bracing treatments, which attempt to reduce or arrest any additional progression, are commonly used in skeletally immature patients who are mildly or moderately affected. In many instances a patient with mild symptoms may simply be monitored to observe if any progression occurs.

Over the last decade, a number of new less invasive surgical interventions have been proposed that seek to stop scoliotic and kyphotic progression without the need for spinal fusion. Such early surgical interventions are, however, only justifiable if significant curvature progression is anticipated. An important variable governing the incremental treatment of such conditions is an accurate progressive history of the spinal curvature. Thus, early detection methods that serve to identify scoliotic curves and kyphosis may greatly assist clinical prognosis and, consequently, improve treatment avenues. Such early detection methods will particularly help in reducing the number of patients presenting to a health professional for the first time with large curves for which a more aggressive treatment is required, considering that early detection at a milder stage could have been treated with a less invasive methods.

Typically the curvature of the spine produced by scoliosis is measured using a scoliometer, a specialized goniometer configured for this purpose. This measuring device spans the spine and is used by placing it over the spine on an individual who is bending forward at a 90° angle. The device provides an indication of the degree of left-to-right tilt as it is moved along the spinal column, which in turn provides a measure of the deformity. Proper use of such a device requires considerable training, as the patient must be positioned properly and the device held vertically throughout measurement. In addition results have to be read and entered manually. As a result reproducibility and accurate tracking of a patient over time are challenging.

Attempts have been made to automate at least portions of this process. In some instances mobile devices (such as smart phones) have been used, as these devices typically include accelerometers that can provide accurate tilt or incline measurements and allow it to act as an inclinometer. For example, U.S. Pat. No. 9,157,738 (to Labelle et al) discusses a device that supports a smart phone and incorporates a lower edge with a "cutout" that accommodates the normal dorsal projection of the vertebrae. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. The smart phone's inclinometer provides a numeric readout of the degree of left-right tilt of the smart phone as the device is moved along the patient's spine. International Patent Application No. WO 2013/126352 (to Franko and Lev) describes a very similar device that is used in conjunction with an app that is run on the smart phone during the patient evaluation and provides a display that mimics the appearance of the traditional scoliometer. Neither device, however, includes measures to insure that they are being used properly. As such they provide, at best, a marginal improvement over traditional instruments. In addition, neither of these devices is useful in the characterization of kyphosis.

Thus, there is still a need for a device that provides simple, accurate, and reproducible measurement of scoliosis and/or kyphosis.

SUMMARY OF THE INVENTION

The following description includes information that may be useful in understanding the present invention. It is not an admission that any of the information provided herein is prior art or relevant to the presently claimed invention, or that any publication specifically or implicitly referenced is prior art.

The inventive subject matter provides devices, systems and methods in which a mobile device that incorporates an inclinometer (for example, a smart phone equipped with an accelerometer) is held within a supporting structure that renders it useful to characterize spinal deformities such as scoliosis and/or kyphosis. Such a supporting structure can include features that secure the mobile device (for example, chamfered surfaces, high friction surfaces, pliant projections, straps, hook and loop enclosures, tensioning devices, detents, etc.) in an upper portion and a lower portion that includes at least one, but preferably two or more rollers or wheels and an interposing, centrally placed cutout or notch dimensioned to permit the assembled device span a typical spinal column. Such rollers or wheels can include encoders (for example, optical, mechanical, and/or magnetic encoders) that provide data related to their rotation, thereby providing a measure of distance travelled as the device rolls. Such a support device can include additional features, such as additional sensors that are accessible by the mobile device, a centrally placed guide (such as a projected LED laser, illuminated filament, flexible bristle, etc) that can be used to keep the assembled device in alignment during use, and supplementary battery power for the mobile device.

In use the assembled device is placed over the spinal column of a subject with the notch over the dorsal vertebral prominences and rolled along all or part of the length of the spinal column, with the accelerometer (e.g., 3 axis, 6 axis, 9 axis, etc) or other sensor (e.g., inclinometer, goniometer, etc) of the mobile device providing data related to its deviation from a selected reference plane during this process. Measurements can be obtained from a subject in either or both of upright and bent forward (e.g., 90°, 45°, etc) positions, and can also be obtained during transition between these positions. Scoliosis can be determined by substantial (e.g. >10°) deviations from the horizontal plane when measurements are made with the subject bending forward at an approximately 90° angle from the waist. Kyphosis can be determined by substantial (e.g., >30°) deviations from an expected angle relative to the vertical plane and/or abnormally sudden changes in the expected angle relative to the vertical plane while standing straight or in transition between standing and bent-forward positions.

The mobile device can include a program or application (e.g. an app) that records data from the accelerometer and/or other sensors (either provided by the mobile device or incorporated into the supporting structure). Such a program or application can display such data for manual recording or, in a preferred embodiment, provide such data to a database. In some embodiments the program or function can include a logic function that processes the data to provide a preliminary diagnosis and/or refer the subject to a medical professional for treatment. It should be appreciated that such processing occurs local to the mobile device (e.g., using mobile device CPU, memory, etc). Alternatively such logic functions can be performed using a separate and distinct CPU that is in communication with the database, for example a cloud based server, laptop device, tablet, etc. In some embodiments the mobile device's program or application can provide additional features, such as displaying information that provides instruction on use of the assembled device and/or providing feedback to a user regarding proper use of the assembled device.

Various objects, features, aspects and advantages of the inventive subject matter will become more apparent from the following detailed description of preferred embodiments, along with the accompanying drawing figures in which like numerals represent like components.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including providing inexpensive, yet accurate and reproducible, methods for early determination of spinal deformities. This in turn permits early and less invasive treatment of such conditions. It should also be appreciated that the low cost and portability of such a testing device permits wide adoption and supports the development of telemedicine applications.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed

BRIEF DESCRIPTION OF THE DRAWINGS

FIGS. 11A-E depict the top, front, side, and top-front-side perspective views, respectively, of yet another embodiment of a testing device of the inventive subject matter.

FIGS. 12A-C depict side, rear, and side perspective views, respectively, of applying a testing device of the inventive subject matter to a patient in a 90° bent position.

FIGS. 12D-E depict a sample plot of lateral tilt against travel distance data and a sample plot of forward tilt against travel distance data, respectively, collected from applying a testing device of the inventive subject matter to a patient in a 90° bent position.

FIGS. 13A-B depict a side view and a close-up view, respectively, of applying a testing device of the inventive subject matter to a patient in a standing position.

FIGS. 14A-B depict sample prior art methods for determining a Cobb angle.

DETAILED DESCRIPTION

Figure 1C:
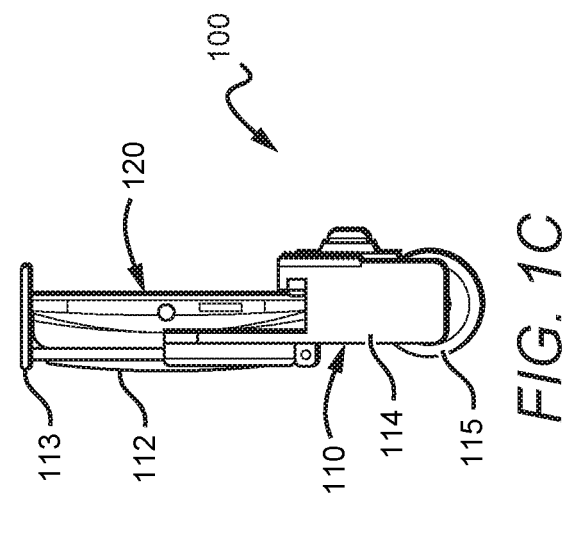
FIGS. 1A-D depict the front, top, side, and top-front-side perspective views, respectively, of an embodiment of a testing device of the inventive subject matter.

The inventive subject matter contemplates devices, systems, and methods for assessing the condition of a spinal deformity. In some embodiments, a supporting structure for a spinal deformity testing device includes an upper portion for securing a computing device (e.g., smart phone, tablet, smart watch, etc), a lower portion with first and second sides opposed to one another, and a lower surface coupled to the first and second sides. Rotatably coupled to the lower surface are one or more rollers (preferably four), with at least a first roller positioned at or near the first side, and a notch interposed between the first and second sides. At least the first roller has an encoder, which preferably provides data related to the distance moved, direction, rolling path, speed, acceleration, relative elevation, or relative rotation (e.g., pivot) of the testing device as it is used.

In embodiments with more than one roller, it is preferred the rollers be evenly divided and positioned between the first and second sides (e.g., two rollers toward the first side, and two rollers toward the second side; one roller toward the first side, and one roller toward the second side, etc). It is contemplated for multi-roller embodiments that each roller has a fixed position on the support structure, and that the relative position of each roller to the other rollers (e.g., distance, angle, elevation, etc) are known and recorded in a computer memory of the support structure or the attached computing device (e.g., smartphone). In multi-roller embodiments with articulating rollers (e.g., caster-wheels, etc), calibration of the relative distance, angle, or elevation with respect to each other wheel is contemplated before using the testing device.

Preferred rollers include wheels (thin, thick, treaded, smooth, etc), though other rolling apparatus are contemplated (e.g., balls, bearings, drums, combinations, etc). It should be appreciated that the type of roller apparatus employed can provide added benefits. For example, where minimal device footprint or contact between the device and a subject (e.g., patient) is desired, thin wheels without tread (e.g., smooth) can be used. Wider wheels or drums can be employed when more contact with a subject is desired, for example where the rollers include massaging textures (e.g., tread, bumps, ridges, other patterns, etc) that relax the muscles around a patient's spine while using the testing device, favorably leading to a more accurate reading of the spine or a more relaxed, pliable subject. Similarly, it should be appreciated the rollers incorporate heating or cooling elements, to further relax or calm the subject. Such calming/relaxing features may be helpful when applying the testing device to irritable or tense patients (e.g., elderly, children, etc) or when applying the device to domestic or wild animals (e.g., Equidae (horses, etc), Suidae (pigs, etc.), Bovidae (cattle, etc), cats, dogs, etc). In the case of ball rollers (e.g., ball-in-socket), it should be appreciated that balls enable multidirectional rolling, and thus provide larger range of motion and increased maneuverability for devices that incorporate balls.

It is contemplated that sensors can be incorporated in testing devices and methods of the inventive subject matter. For example, sensors (e.g., accelerometer, gyroscope, magnetometer, camera, heat sensor, infrared sensor, pressure sensor, electro-optical sensor, X-ray sensor, acoustic sensor, inclinometer, goniometer, scoliometer, etc) can be incorporated into the support structures described above, can be part of a computing device (e.g., smartphone, etc), or can be added (e.g., physically coupled, communicatively coupled, etc) to the support structure or the computing device (e.g., via USB port, Bluetooth, etc). It should be for embodiments of the inventive subject matter designed to use sensor-rich smart phones, fewer sensors are needed in the support structure, thus reducing maintenance and cost of such support structures.

It is contemplated that the support structures and computing devices of the inventive subject matter are communicatively coupled (e.g., communication link). For example, a smartphone can have a wired communication link with the support structure (e.g., USB cable, etc) a wireless communication link (e.g., a wireless protocol, a Wi-Fi transmitter, a Wi-Fi receiver, a Bluetooth transmitter, a Bluetooth receiver, a ZigBee transmitter, a near field transmitter, a near field receiver, a radio frequency transmitter, a radio frequency receiver, an infrared transmitter, an infrared receiver, etc), or both.

The inventive subject matter further includes methods for characterizing a condition of a spinal deformity in a subject (e.g., person, animal, models, mechanical devices, etc). While the subject is in a first position (e.g., prone, standing, bent at 90°, tense, relaxed, etc), a testing device as described above is placed at a first starting position along the subject's spine (e.g., near the gluteal cleft), such that the notch of the testing device is centered on the spine. The testing device is then moved (e.g., pushed, rolled, etc) along the spine on the first roller. While moving the testing device along the spine, a first dataset is collected related to a distance traveled by the encoder associated with the first roller and at least one (preferably both) of (1) data related to a first lateral tilt of the testing device (or spine) or (2) data related to a first forward tilt of the testing device (or spine). While the subject is in a second position (e.g., prone, standing, bent at 90°, tense, relaxed, etc) that is different than the first position, the testing device is placed at a second starting position along the subject's spine (e.g., near the gluteal cleft), such that the notch of the testing device is centered on the spine. The testing device is then moved (e.g., pushed, rolled, etc) along the spine on the first roller. While moving the testing device along the spine, a second dataset is collected related to a distance traveled by the encoder of the first roller and at least one (preferably both) of (1) data related to a second lateral tilt of the testing device (or spine) or (2) data related to a second forward tilt of the testing device (or spine).

While the first and second datasets collected include data related to first and second distances traveled by the encoder, it should be appreciated additional data can be collected. For example, it is contemplated that the movement (e.g., direction, speed, acceleration, elevation) of the device is collected by encoders associated with rollers of the device. Viewed from another perspective, the device tracks its path of movement along the spine of the patient, such that the subject's spine is mapped in three dimensions and can be rendered in various 3D models.

At least part (preferably all) of the first and second datasets (e.g., data related to the first and second distance traveled and at least one (preferably both) of (1) the first and second lateral tilt or (2) the first and second forward tilt, other combinations, etc) are provided to a database. At least some (preferably all) of the data thus provided (e.g., the first or second lateral tilt, the first or second forward tilt, combinations, etc) is compared to a first stored value to determine the condition of the spinal deformity. A report related to the condition of the spinal deformity is generated, wherein the condition is one of (1) presence of a scoliosis deformity, (2) presence of a kyphosis deformity, or (3) absence of a scoliosis or kyphosis deformity in the subject. It is contemplated that presence of a scoliosis deformity is determined when either (preferably both) of the first or second lateral tilt exceeds a threshold (e.g., 5°, 7°, 8°, 9°, 10°, 11°, 12°, 13°, 14°, 15°, 20°, 25°, 30°), preferably 10°. In some embodiments, the lateral tilt of the subject's spine is measured again (e.g., third, fourth, fifth lateral tilt, etc), and a scoliosis deformity is determined when the average of the lateral tilts measured (e.g., first, second, third, fourth, fifth, etc) exceeds a threshold. It is contemplated that the lateral tilt of the subject's spine can be measured periodically (3/day, 2/day, 1/day, 4/week, 3/week, 2/week, 1/week, 4/month, 3/month, 2/month, 1/month, etc). In such embodiments, it is contemplated the data analyzed can be limited to the most recent measurements/readings be analyzed (e.g., prior week, prior 3 days, prior 2 days, last 5 readings, last 4 readings, last 3 readings, last 2 readings, etc), or weights be applied to at least some of the measurements/readings (e.g., higher weight for last 3 readings, last 2 readings, last reading, lower weights for oldest 5 readings, oldest 3 readings, oldest reading, etc).

In a similar fashion, presence of a kyphosis deformity is determined when either (preferably both) of the first or second forward tilt exceeds a threshold (e.g., 20°, 25°, 27°, 28°, 29°, 30°, 31°, 32°, 33°, 34°, 35°, 40°, 45°, 50°), preferably 30°. It is contemplated the forward tilt of the spine can be measured further, the measurements/readings can be averaged, or the measurements/readings can be weighted as described above. In preferred embodiments, at least some (preferably all) of the lateral tilt measurements and the forward tilt measurements are used by the mobile device (or cloud server) to construct a model (e.g., digital) of the subject's spine. In preferred embodiments, a digital image of the subject's back (e.g., dorsal view) is acquired and used in part to determine the condition of the spinal deformity or to construct a model of the spine.

In some embodiments the testing device instructs the subject to seek medical attention when the report indicates a scoliosis deformity or a kyphosis deformity. The device can also transmit the report to a medical professional. Reports generated by the device can further include or rely upon a relationship between the first distance traveled and at least one of the first lateral tilt or the first forward tilt, preferably both. Further, the reports can include or rely upon a relationship between the second distance traveled and at least one of the second lateral tilt or the second forward tilt, preferably both. In preferred embodiments, the report incorporates all, or at least some, of the datasets collected by the device for a specific subject over a specified time period.

One embodiment of the inventive concept is shown in FIGS. 1A-D as device 100. In such an embodiment, upper portion 112 of supporting structure 110 includes tensioning arm 113, which permits the supporting structure to adjustably secure mobile devices of different dimensions and configurations, here mobile device 120. High friction materials (in the form of pliant plastic foam, rubber, etc) can also be provided to further secure mobile device 120. As shown lower portion 114 of the supporting structure includes two rollers, wheels 115 and 116, with one wheel being placed near each of the lower corners of lower portion 114.

Such rollers can include encoding features (such as optical, mechanical, and/or magnetic encoders, not pictured) that provide quantitative information regarding the rotation of the wheel or roller, and thereby provide a measure of distance travelled by device 100. This in turn provides a clinician with the location of the deformity along the spinal column. Such encoders can also provide information related to the speed and/or acceleration of the assembled device when in use. Such data can be used to monitor use of device 100 and insure that it is being used appropriately (for example, by providing an alarm or other warning when speed and/or acceleration fall outside of predetermined limits). Centrally placed between wheels 115 and 116 along lower portion 114 is notch 117, which is shaped to permit easy passage of a typical spinal prominence during use. Notch 117 has an arcuate shape, and it is contemplated such notches typically have a height of from about 0.5 cm to about 2.5 cm. Device 100 further has guide feature 118 centrally placed immediately above notch 117. Guide feature 118 can be seen as a raised arrow shape, but can also or alternatively include a laser diode or similar device (for example, a device that provides an orienting and/or guiding optical or visual effect), which projects a beam of light downwards towards the spine during use, and aids in positioning of device 100.

It should be appreciated that providing positional information in association with lateral and/or forward tilt in devices and methods of the inventive concept provides substantial benefits not realized in the prior art. For example, association of distance traveled along the spine with a degree of lateral and/or forward tilt can provide a clinician with information related to the position of a spinal deformity, and complements traditional photographic and radiographic information. In addition, speed and/or acceleration data collected during use can be utilized to verify proper utilization of the assembled device and to insure the integrity of the gathered data. For example, speed data indicating that the assembled device is being moved along the spine too quickly (e.g. when data related to the rate of roller or wheel rotation exceeds a predetermined value) can trigger an alarm or warning to the user (e.g. a prompt to repeat the measurement). Alternatively, software running on the mobile device can refuse to enter data from an assembled device until it used properly. To aid in this, such software can display a speed indication while the assembled device is in use.

As noted above, lower portion 114 of supporting structure 110 can include additional sensors, circuitry, and/or a battery. Suitable additional sensors include a high resolution accelerometer, a temperature sensor, an infrared sensor, pressure sensor, and/or a camera. Such sensors can be used to replace, supplement, and/or calibrate sensors provided on mobile device 120. For example, an accelerometer on lower portion 114 of supporting structure 110 can be used to verify or correct (e.g. through calibration) an accelerometer of mobile device 120. This advantageously permits the use of a variety of mobile devices from different manufacturers, which may utilize accelerometers and/or other sensors with different ranges and/or degrees of sensitivity.

Figure 1D:
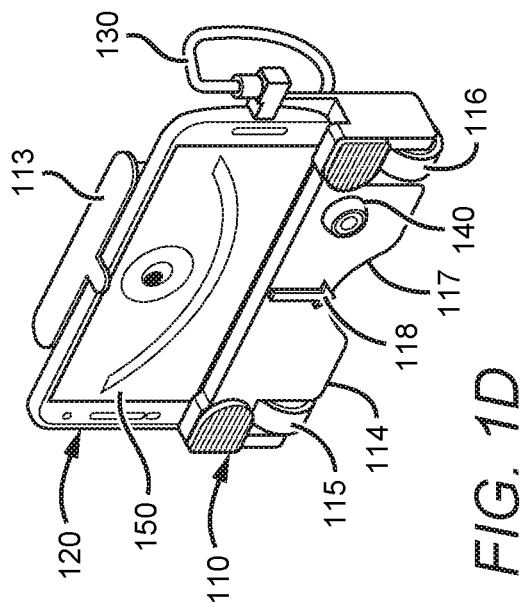

Alternatively or in combination, sensors of supporting structure 110 can be used to verify data collected by sensors of mobile device 120. As shown support structure 110 can also include cable 130 that interfaces with a data and/or power port of mobile device 120. It should be appreciated, however, that other mechanisms (e.g. WiFi, Bluetooth, near field transmission) can be used to transfer data between supporting structure 110 and mobile device 120. FIG. 1D provides an orthogonal view of device 100, and additionally shows button 140 that provides a visual indication of the power status of device 100. Such a button can also provide control functions for device 100. For example, button 140 can be pressed at the start of a diagnostic procedure to signal device 100 to begin collecting data and again at the end of the diagnostic procedure to signal device 100 to cease data collection.

Figure 1A:
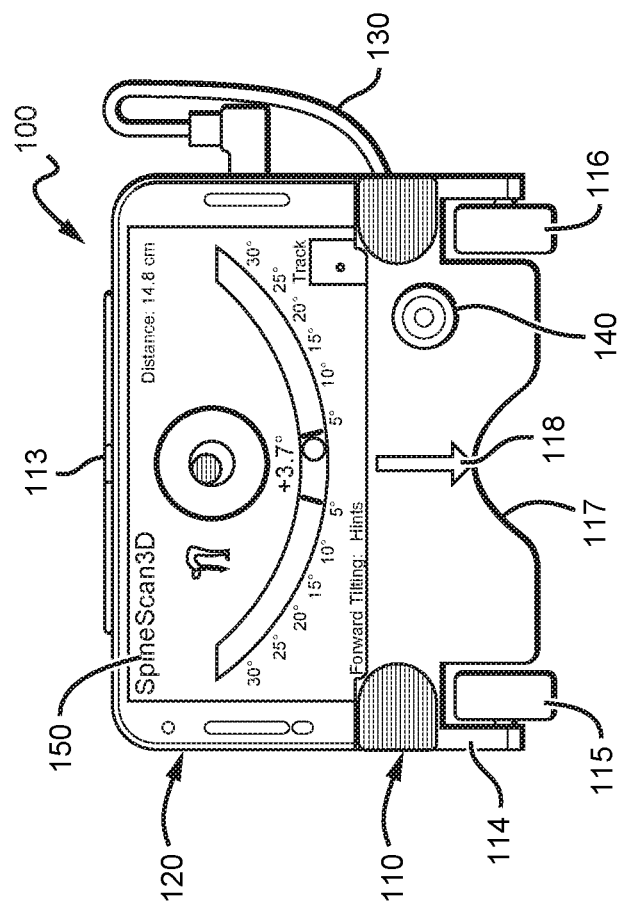
Figure 1B:
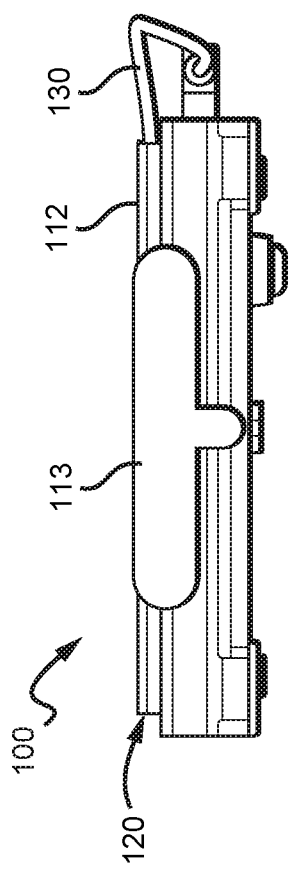
Figure 2C:
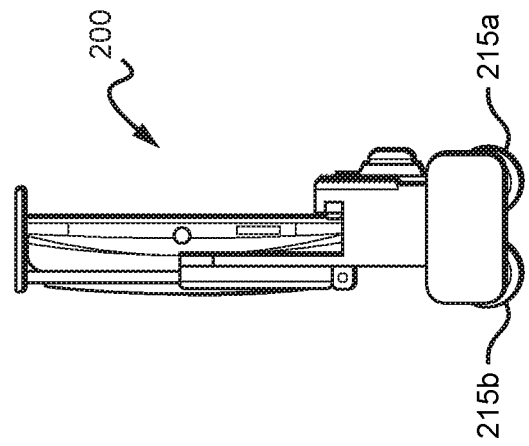
FIGS. 2A-D depict the front, top, side, and top-front-side perspective views, respectively, of another embodiment of a testing device of the inventive subject matter.
Figure 2D:
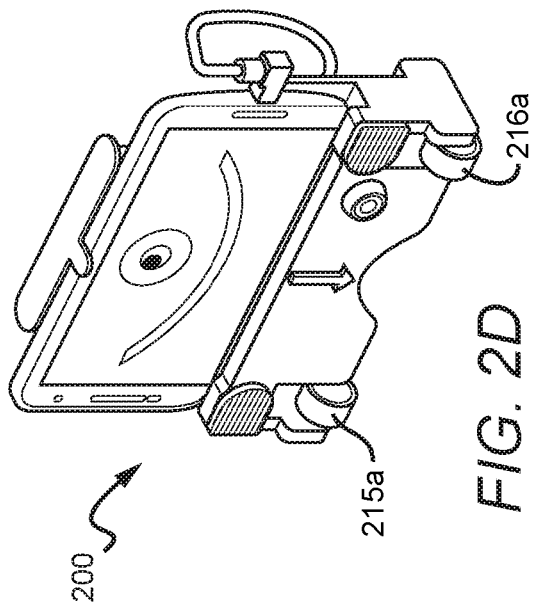
Figure 2A:
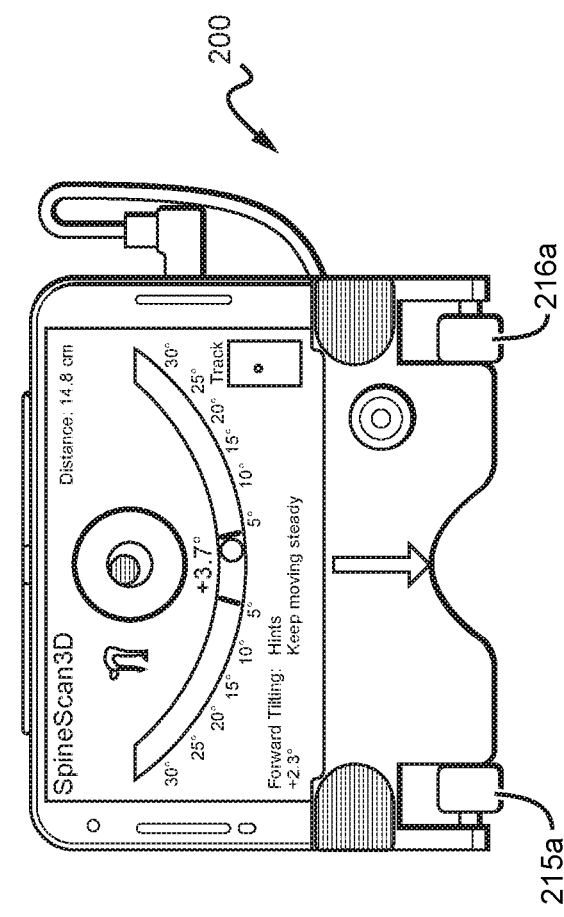
Figure 2B:
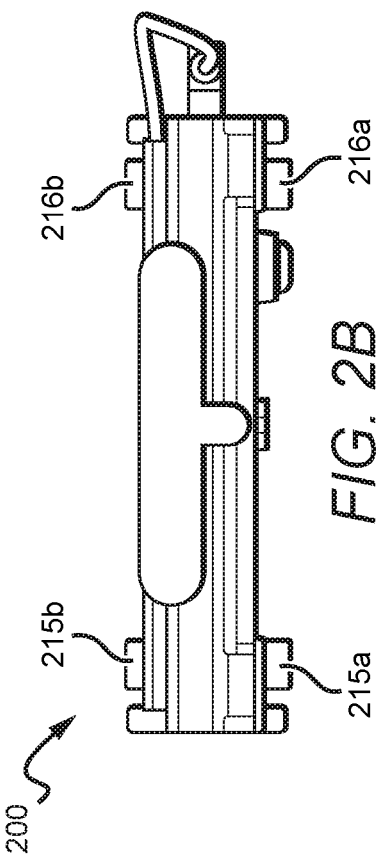

Both FIGS. 1A and 1D depict an embodiment of display 150 provided by a program or application (here, SpineScan3D) via mobile device 120 when in use. As shown, both graphic and numeric displays provide information related to the degree of lateral tilt being experienced by the assembled device. Information related to the distance traveled by the device can also be displayed. The program or application can also provide feedback to a user indicating that the assembled device in the form of a display feature having a pair of concentric circles in fixed positions and a dynamically updated icon (for example, a color coded, filled circle) that provides an indication of proper or improper use. For example, the position of such an icon within an indicated acceptable range of positions can indicate proper use. This can be supplemented by color coding, for example displaying a green color for proper use. Deviation of device 100 from proper positioning can be indicated by moving such an icon outside of the indicated acceptable range, which can be supplemented by changing color (for example, from green to red). In some embodiments this can be further supplemented by an audible alarm or alert.

In another embodiment, depicted in FIGS. 2A-D, device 200 largely shares the elements of device 100, but differs in that device 200 includes four rollers, wheels 215a, 215b, 216a, and 216b, arranged as pairs of rollers located at or near each of the lower corners of the lower portion of the supporting structure. In such an embodiment, one or both of each pair of wheels (e.g., 215a-b and 216a-c) can include encoding features (such as mechanical, optical, and/or magnetic encoders) that provide a measurement of the distance that the device has traveled during use. Further, for embodiments such as device 200 with more than two rollers, it is contemplated the relative distance between each roller with respect to each other (e.g., wheel base) is known and recorded in a computer memory (e.g., RAM) of the supporting structure, the mobile device, or in a database accessed by the application on the mobile device.

While the embodiments shown in FIGS. 1A-D and FIGS. 2A-D depict the mobile device secured in a position that is essentially perpendicular to the plane defined by the wheels or rollers of the supporting structure, it should be appreciated that in some embodiments the mobile device can be secured in a plane that is essentially parallel to that of the wheels or rollers. Such an orientation is useful for characterizing the shape of the spinal column while the individual being tested is standing in an upright position or transitioning between upright and forward-leaning positions. In some embodiments this can be accomplished by incorporating a joint or hinge at the juncture of the lower and upper portions of the supporting structure. Such a joint or hinge mechanism can include one or more stops that fix the mobile device at the desired angle relative to the rollers or wheels. In a preferred embodiment the mobile device can be secured at an angle that places it parallel or nearly parallel to the plane defined by the rollers or wheels. In other embodiments the upper portion of the supporting structure is arranged such that the mobile device is held in this position. Such an embodiment is depicted in FIGS. 3A-D, where device 300 largely has the elements as described in FIGS. 1A-D and FIGS. 2A-D.

Figure 3C:
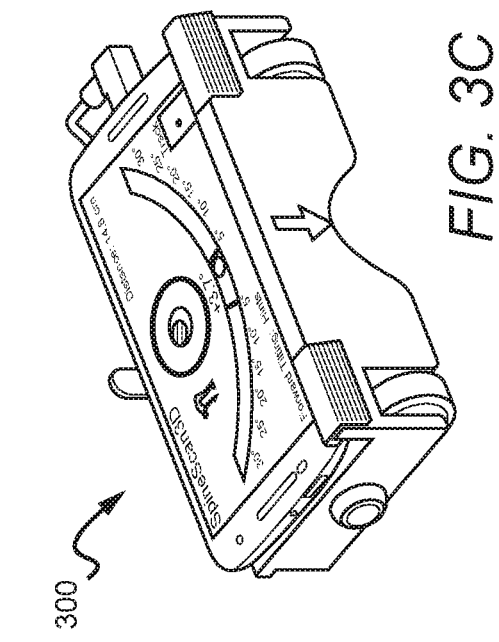
FIGS. 3A-E depict the top, front, side, top-front-side, and bottom perspective views, respectively, of yet another embodiment of a testing device of the inventive subject matter.
Figure 3D:
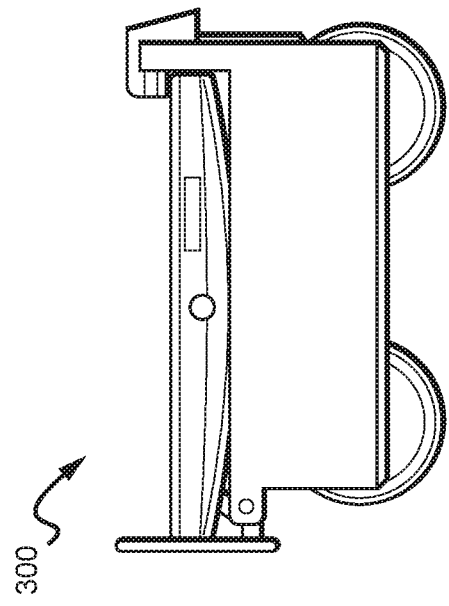
Figure 3A:
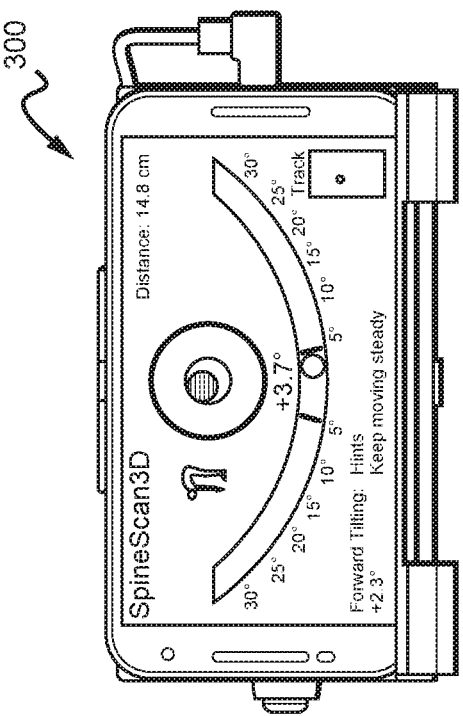
Figure 3B:
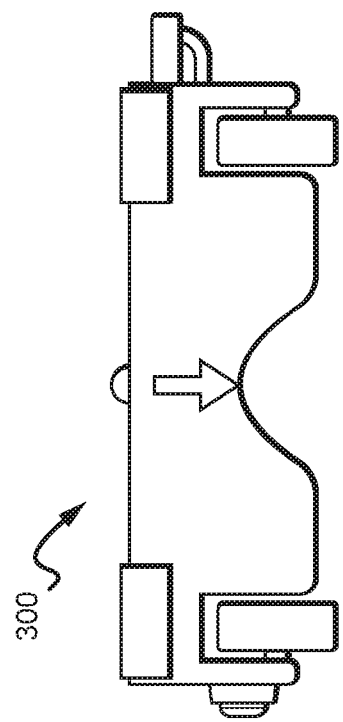
Figure 3E:
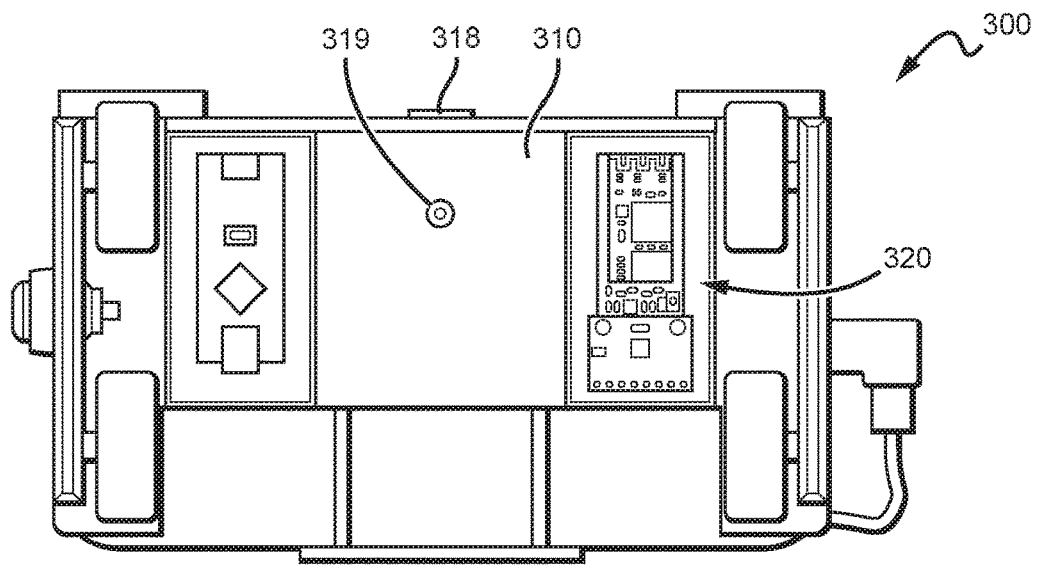

FIG. 3E further depicts a bottom view of device 300. In this view, LED laser 319 can be seen along bottom surface 310, which is in line with guide feature 318 (as described for guide feature 118 in FIGS. 1A-D). Further, printed circuit board 320 is depicted, which provides additional circuitry and sensors for the supporting structure as described above (e.g., accelerometer, gyroscope, magnetometer, camera, heat sensor, infrared sensor, pressure sensor, electro-optical sensor, X-ray sensor, acoustic sensor, inclinometer, goniometer, scoliometer, etc).

Figure 4:
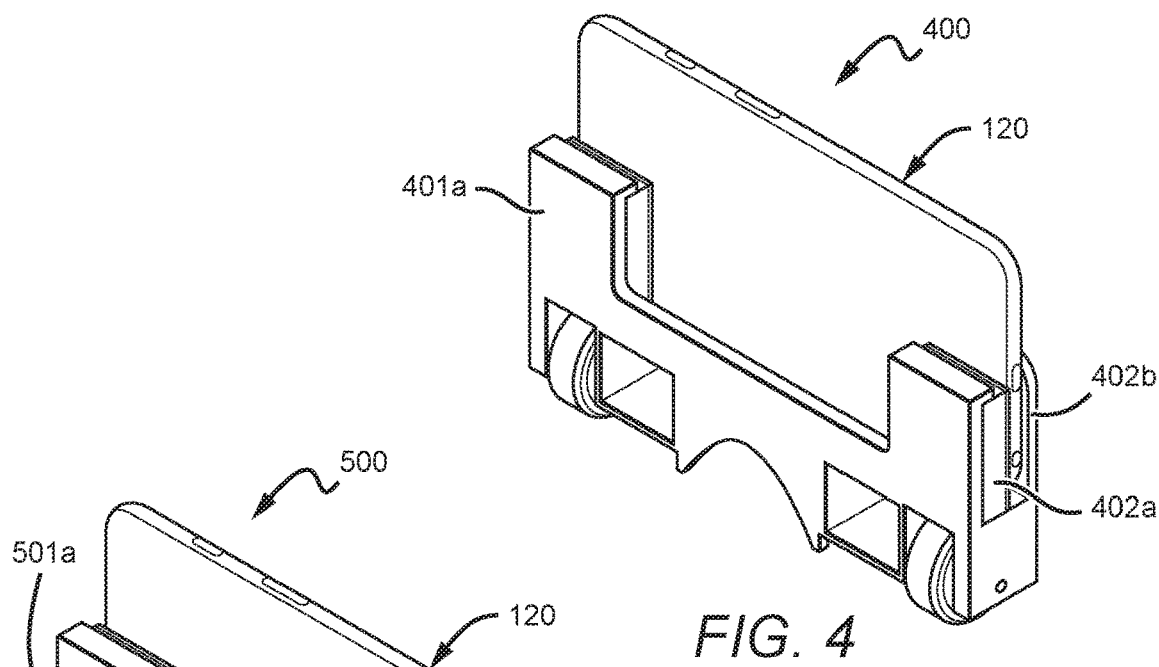
FIG. 4 depicts the top-front-side perspective view of still another embodiment of a testing device of the inventive subject matter.

FIG. 4 depicts device 400, which largely shares the elements for device 100 in FIGS. 1A-D. Device 400 differs from device 100 at least in that device 400 does not include a guide feature (118 in FIGS. 1A-D) and does not include an upper portion (112) or a tensioning arm (113) as depicted in FIGS. 1A-D. Rather device 400 includes cradle portions 401a-b (401b not pictured) and 402a-b, which are positioned opposite each other and on other side of mobile device 120. Thus, cradle portions 401a-b and 402a-b serve to secure mobile device 120 in place (e.g., removably couple) with device 400.

Figure 5:
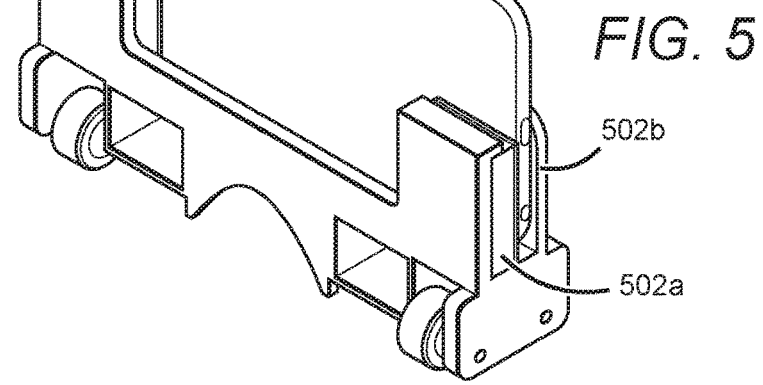
FIG. 5 depicts the top-front-side perspective view of a further embodiment of a testing device of the inventive subject matter.

Similarly, FIG. 5 depicts device 400, which largely shares the elements for device 200 in FIGS. 2A-D. Device 500 differs from device 200 at least in that device 500 does not include a guide feature and does not include an upper portion or a tensioning arm a. Rather device 500 includes cradle portions 501a-b (501b not pictured) and 502a-b, which are positioned opposite each other and on other side of mobile device 120. Thus, cradle portions 501a-b and 502a-b serve to secure mobile device 120 in place (e.g., removably couple) with device 500.

Figure 6:
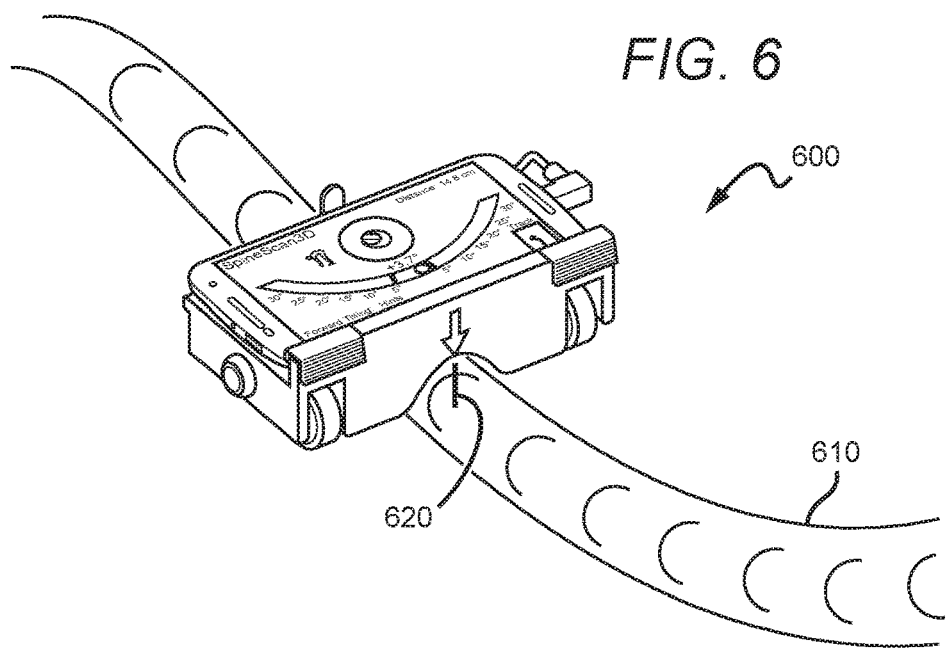
FIG. 6 depicts the application of a testing device of the inventive subject matter to a mock spine.

FIG. 6 depicts an example of testing device 600 (i.e. supporting structure and mobile device) as described above for FIGS. 3A-E (and reference to FIGS. 1A-D and 2A-D). Here, testing device 600 is superimposed on example spinal column 610 of a subject being tested. As shown, light beam 620 is used to aid a user in keeping the device centered over spine 610 as it is moved. Spinal deformities resulting in twisting of the spine cause device 600 to pivot as it is moved, resulting in lateral tilt detected by testing device 600.

Figure 7:
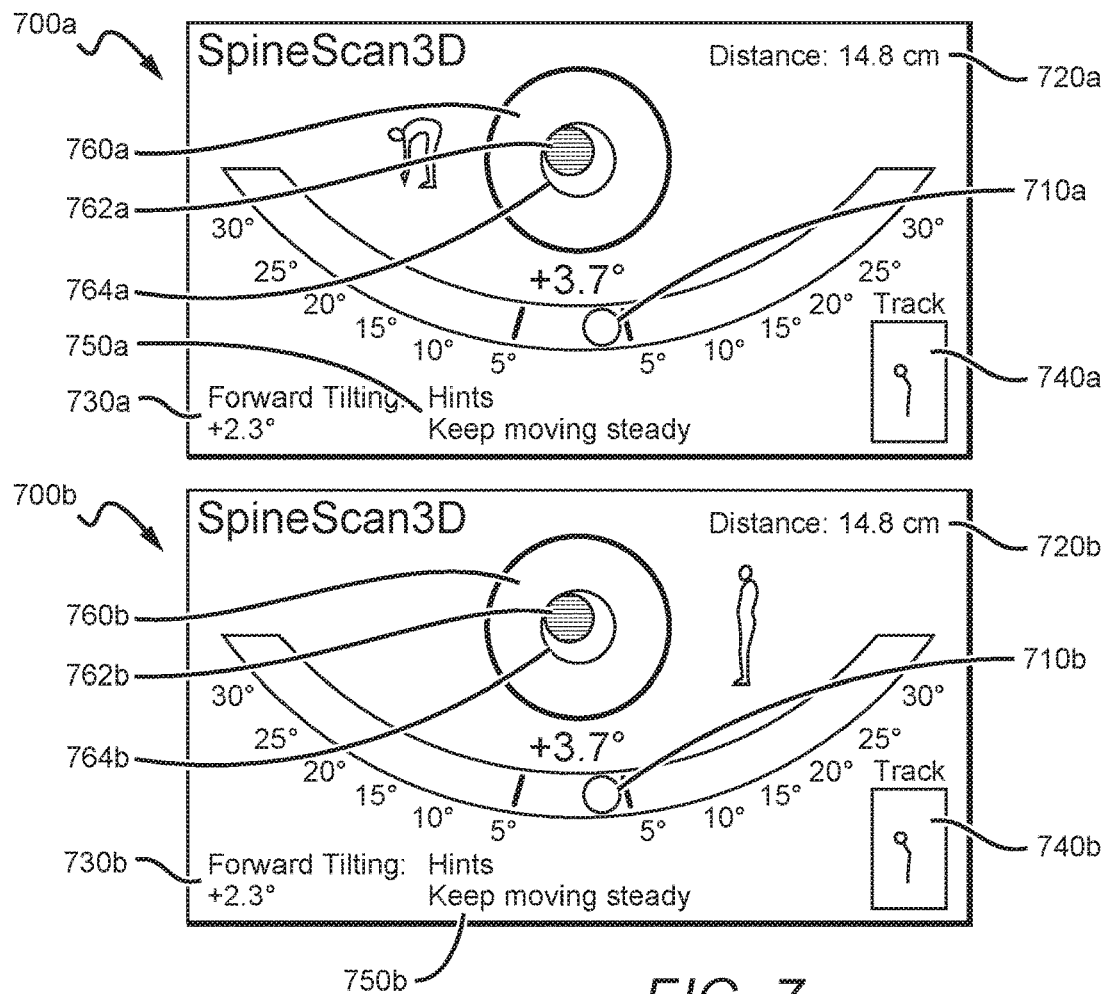
FIG. 7 depicts a graphical user interface of a testing device of the inventive subject matter in a state.
Figure 8:
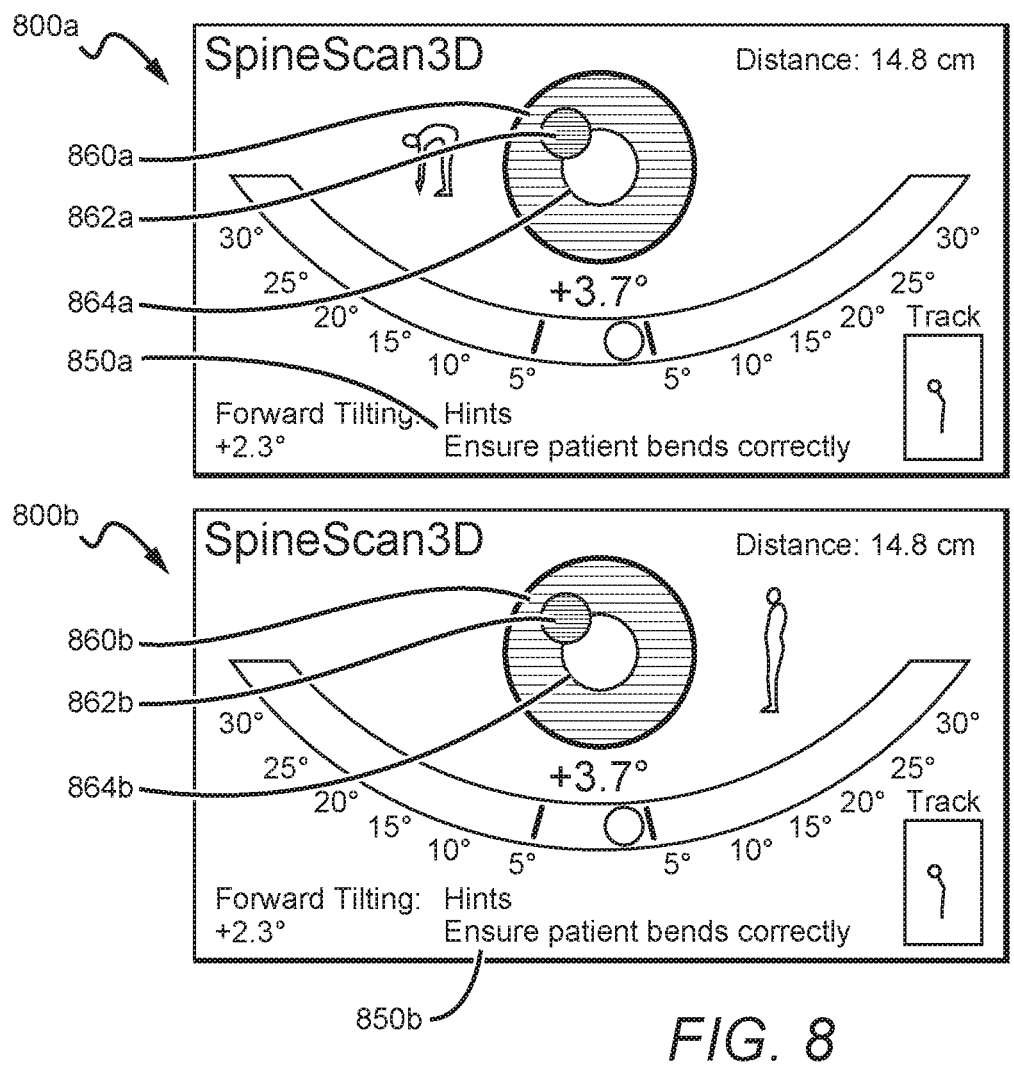
FIG. 8 depicts a graphical user interface of a testing device of the inventive subject matter in another state.
Figure 9:
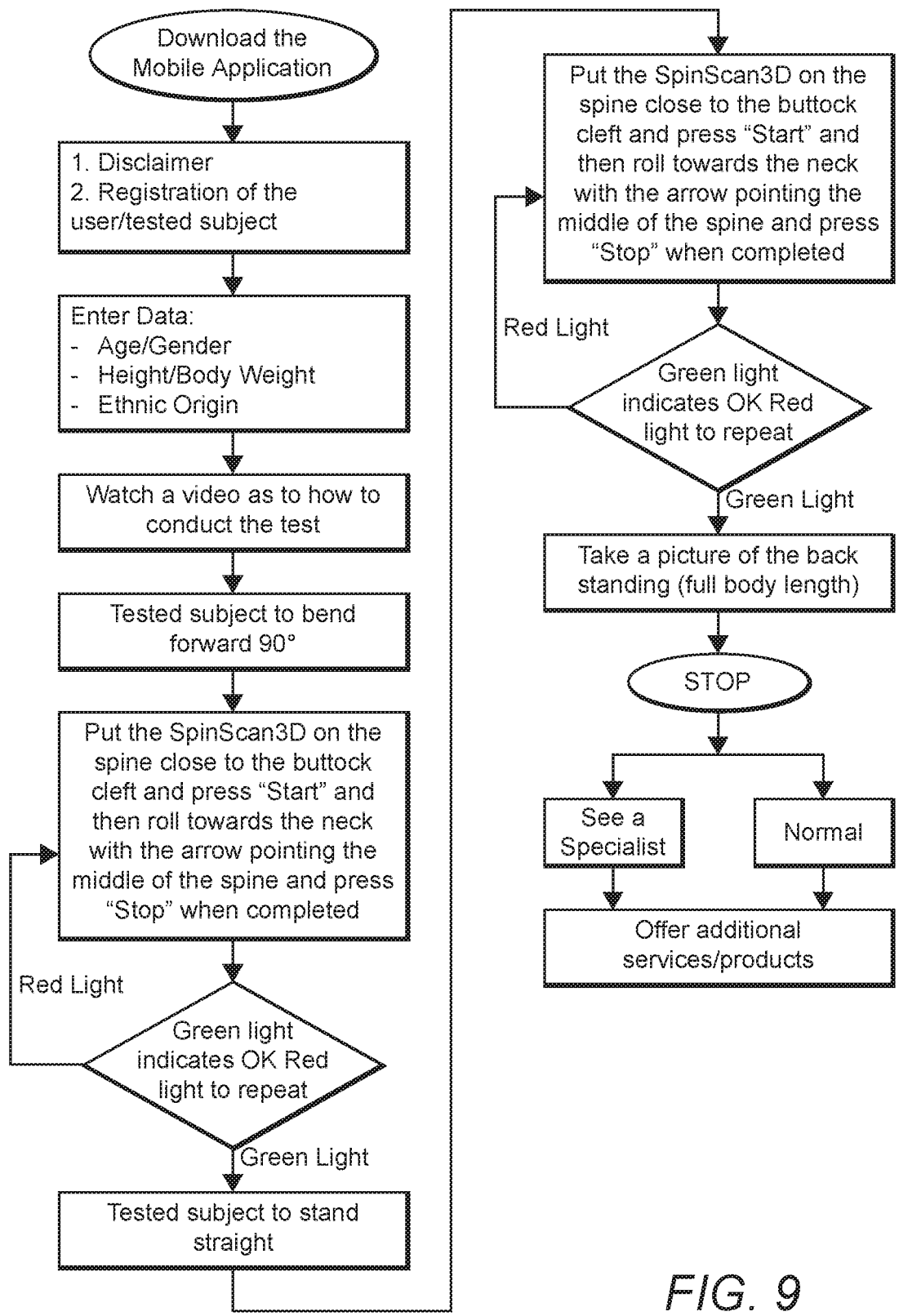
FIG. 9 depicts a flowchart of a mobile device application of the inventive subject matter.

FIGS. 7 and 8 depict examples of displays 700a-b and 800a-b provided by SpineScan3D software during use. FIG. 7 depicts examples of displays provided during proper use of the device when the subject is standing and when the subject is leaning forward at an approximately 90° angle. As shown, the display provides information related to the lateral tilt angle (710a-b) of the test device, and can also provide information related the distance (720a-b) that the test device has been used, the degree of forward tilt (730a-b) of the test device, a graphical depiction of the track (740a-b) followed by the testing device, and prompts (750a-b) for the user. Among such prompts is an indicator (760a-b) that the testing device is being positioned and used properly. This is in the form of a set of concentric circles and a dynamically updated icon. In FIG. 7 proper use is being indicated by both the position of the icon (762*a-b*) (e.g. within the "target" smaller circle (764*a-b*)) and an indicating color (green). Such a display can also provide additional prompts, for example hints for the user regarding proper use (in this instance "keep moving steady") and a graphical depiction of the proper orientation of the subject during the testing process (for example, differentiating between standing and bending positions). FIG. 9 depicts such a displays 800*a-b* when the test is being performed improperly. In this instance the display provides warnings in the form of an icon (862*a-b*) that lies outside of the target range (i.e. the smaller circle (864*a-b*)) and a warning color (red) (860*a-b*). In addition prompts provide direction to the user for correction of the issue (850*a-b*).

As noted above, embodiments of the inventive concept can include software (such as programs or applications) that are configured to run on the mobile device and serve to assist a user in performance of the test and/or recording of the results. An example of a flow diagram for such software is shown in FIG. 9. As shown, following installation of the software on the mobile device, starting such an application can first provide a disclaimer regarding use of the testing device and interpretation of results, along with providing an opportunity to enter information that identifies the user and/or the test subject. Such software can also allow for the entry of subject-specific data, for example age, gender, height, body weight, BMI, ethnic or national origin, known medical conditions, family history, medications being taken, current physician, and/or insurance information. Such software can also provide (or provide a link to) an instructional video that demonstrates proper use of the device. In some embodiments the software can provide for verification on the part of the user that such instruction has been viewed and understood. Testing can be performed with the subject in a bent-forward position (i.e. at approximately 90°) position, standing straight, both positions, and/or in transition between these positions. In the example shown testing is first performed in the bent-forward position. The assembled testing device is placed near the gluteal cleft, with the notch of the device centered over the spine. Testing is initiated by pressing "start" and moved along the spine toward the neck while keeping the guide featured centered over the spine, and halted by pressing "stop". During use a green indicator on the display indicates that testing should continue, whereas a red indicator on the display indicates that at least a portion of the test needs to be repeated.

At the completion of the first portion of the test the subject is instructed to assume the next test position (in this instance, standing) and the process is repeated. In preferred embodiments, when testing is taken of a subject in a standing position, the device is placed at the at the base of the subject's neck (e.g., T1 of thoracic vertebrae, etc) and moved downward along the subject's spine toward the gluteal cleft (see, e.g., FIG. 13A). It should also be appreciated that tests of a subject in a 90° bend, a standing position, or any angle there between, can start by placing the device at the base of the subject's neck (e.g., T1 of thoracic vertebrae, etc) and moving along the spine toward the gluteal cleft, or start by placing the device near the gluteal cleft and moving along the spine toward the subject's neck When testing in the last position is complete a camera of the mobile device (or, alternatively, of the supporting structure) can be used to take a digital image of the subject's back while standing. In some embodiments of the inventive concept, a pair of cameras (for example, a pair of cameras provided on a mobile device or a camera of the mobile device and a camera of the supporting structure in combination) can be used to generate a three dimensional image of the subject's back. This image can be reviewed manually or subjected to image recognition software in order to provide additional data about the subject's condition. Data gathered during the testing process can be stored in a local database or transferred to an offsite database, and analysis performed (as described below) to determine of the results are normal or require further evaluation. In the event that the results are abnormal the testing device can display a prompt indicating that a visit to a medical professional (for example, an orthopedic specialist) is needed.

Figure 10:
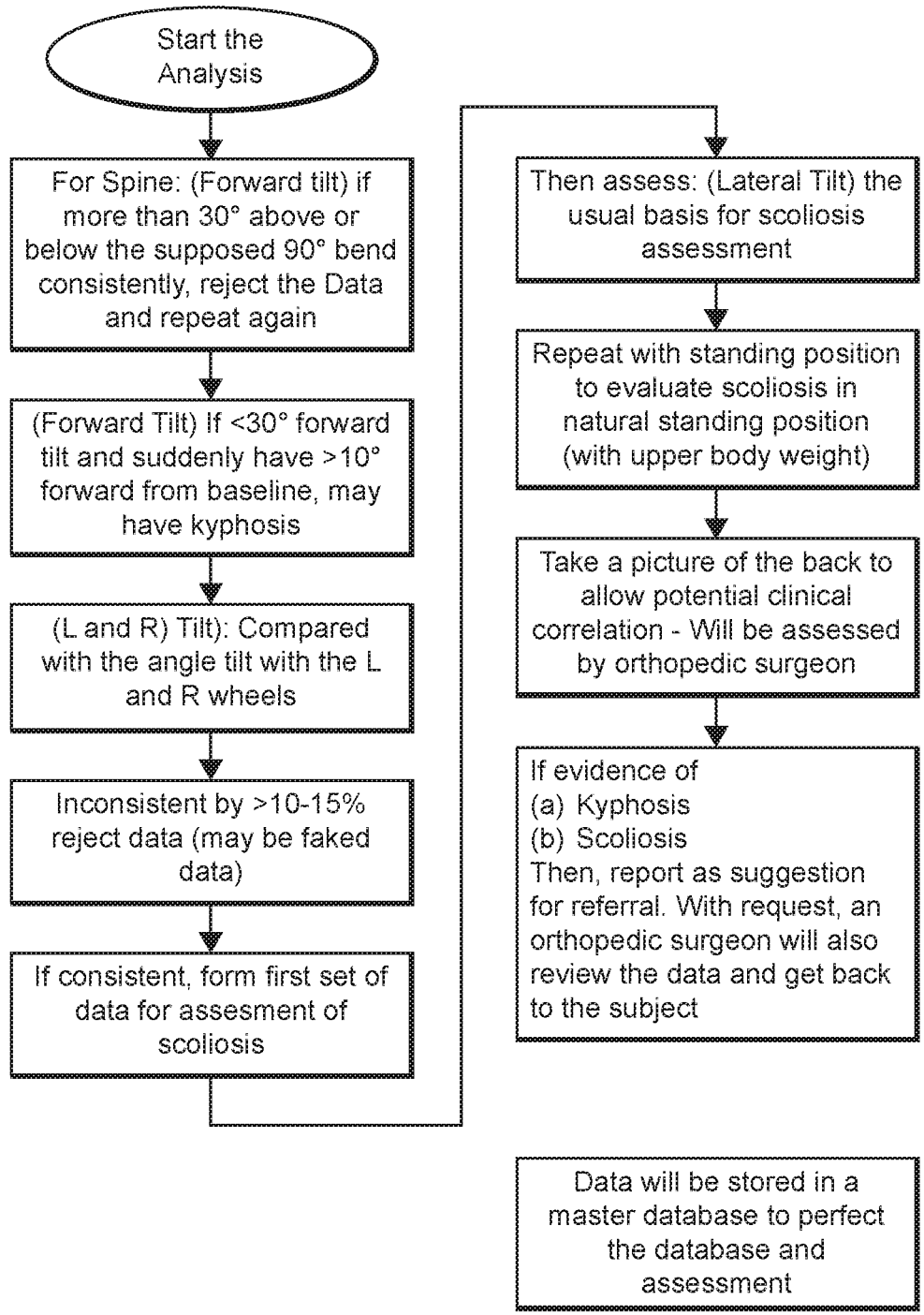
FIG. 10 depicts a flow diagram of an analytical algorithm of the inventive subject matter.

As noted above, embodiments of the inventive concept can include software that applies logic to data gathered as shown in FIG. 9 above to determine if the subject has a significant spinal deformity. An example flow chart for such a process is shown in FIG. 10. As shown, after analysis is initiated results are initially interrogated for improper positioning of the subject (for example, having a >30° from the desired 90° in the bent-forward position). Determination that the testing position was improper can result in rejection of the results and a prompt to repeat the testing. Data related to the forward tilt (i.e. tilting in the coronal plane) that exceeds a predetermine amount (for example, 30°) or that shows a sudden change (for example, a sudden change of >10°) can provide a determination of kyphosis. Tilt between the left and right wheels (i.e. lateral tilt) of the testing device can be used to make a determination related to scoliosis. In order to verify that the data is accurate and/or genuine, a measure of the consistency of the data can be made, with inconsistency exceeding a certain amount (e.g. 10%) being used to reject the data. For example, data related to lateral tilt and/or forward tilt that shows rapid changes (for example, exceeding a predetermined limit for change in angle over a given distance) can trigger a prompt to a user of the assembled device to repeat the measurement. Alternatively, differences in the distance traveled between left and right rollers/wheels can be correlated with changes in lateral tilt to verify that the measured lateral tilt is due to a spinal curvature (as opposed to improper handling of the instrument). Data that is determined to be consistent can be used for diagnostic purposes. Such consistent data can be assessed by comparing the measured degree of lateral tilt with current clinical guidelines. For example, a lateral tilt that exceeds 10° can be considered indicative of scoliosis. In some embodiments the degree of lateral tilt can be used to grade the degree of scoliosis and/or severity of the deformity. In other embodiments the clinical guidelines used in such a determination can be dynamically updated in the testing software as these guidelines evolve. Testing performed in the leaning-forward position can be repeated in the standing position and similarly evaluated, and such testing can be performed by acquiring one or more digital images of the subject's spine (which can be assessed by a clinician). Such images can be used to derive a correlation between measurements made by the testing device and the clinical presentation of test subjects. Testing software logic can further generate a prompt that suggests referral to an appropriate specialist if evidence of scoliosis and/or kyphosis is found. In a preferred embodiment of the inventive concept such data is stored in and/or transmitted to a database. Such accumulated data can be used to modify and further improve the performance of the diagnostic algorithm, for example through correlation to clinical assessment by medical professionals and/or clinical outcomes.

Figure 18:
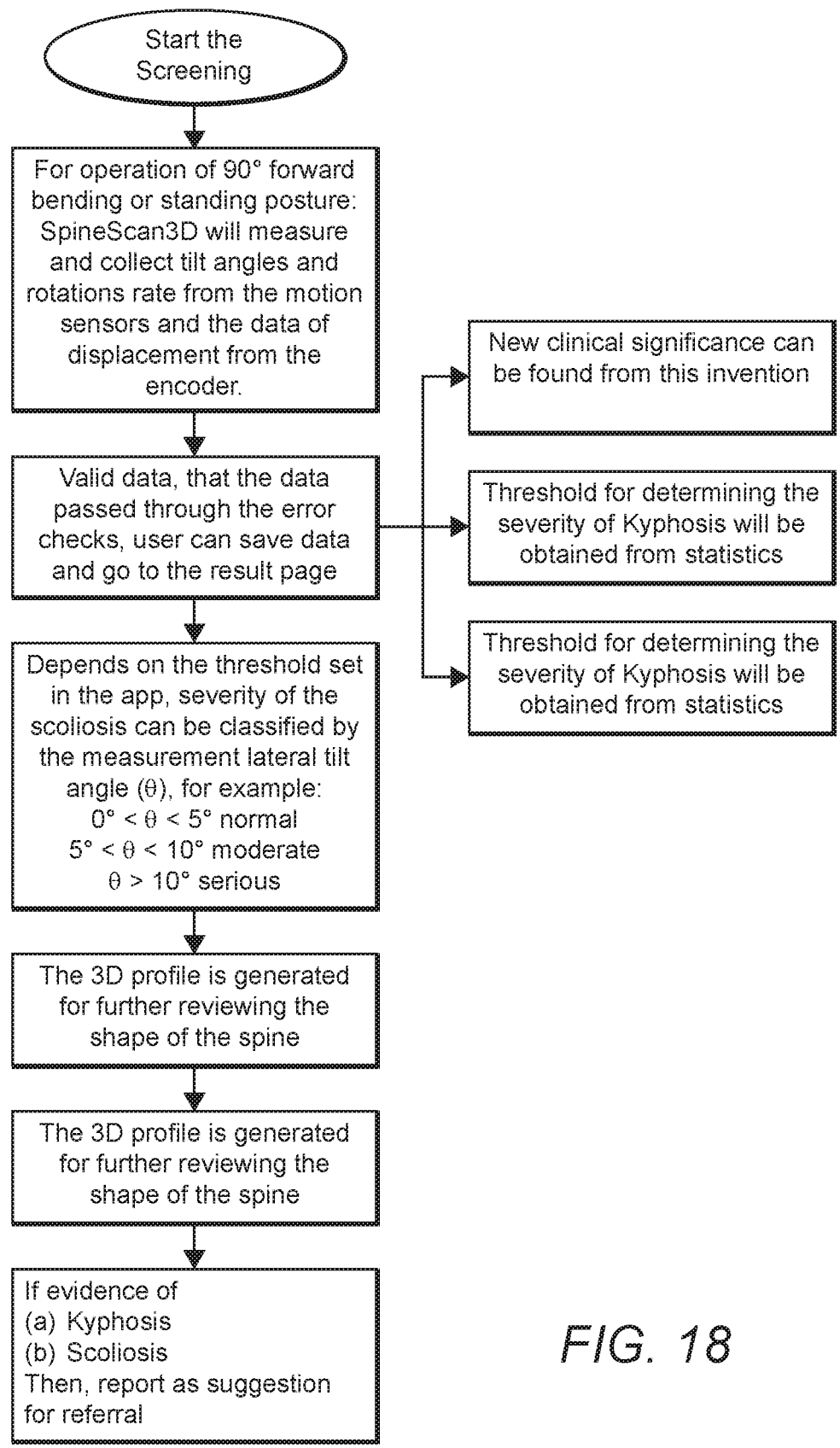
FIG. 18 depicts another flowchart of a mobile device application of the inventive subject matter.

An additional example flow chart for such processes is depicted in FIG. 18. As can be seen, screening is started with a patient in either a 90° forward bending or a standing posture. A device of the inventive subject matter is used to measure and collect tilt angles and rotation rates from the sensors on the device as well as the data from encoders on the device. The collected data is validated, for example by passing the data through error filters (e.g., inconsistent with prior results, reading not physically possible, etc), and the user is given the option to save the collected data and proceed to a results page. Depending on thresholds set in the mobile application, severity of the scoliosis or kyphosis can be classified by the measured lateral tilt angle or forward tilt angle. For example, for scoliosis, a lateral tilt angle of 0°-5° can be set as a normal range, 5°-10° can be set as a moderate range, and >10° can be set as a serious range, while for kyphosis, a forward tilt angle change of 0°-10° can be set as a normal range, 10°-15° can be set as a moderate range, and >15° can be set as a serious range. It should be appreciated that the ranges can be set by the user, or alternatively can be derived from statistical analysis of patient data (e.g., demographic data, data compiled by devices of the inventive subject matter, derived from clinical databases, derived from predictive computer models, etc). The collected data can be further analyzed to produce a 3D profile of the subject's spine to further visualize and review the shape of the spine. Such generation can be automatically performed by mobile applications of the inventive subject matter, or may be performed using cloud based servers. If the 3D model or the set tolerances indicate that a subject exhibits evidence of kyphosis or scoliosis, then a report can be issued to the subject instructing referral to a medical professional.

As shown in FIGS. 11A-E, in some embodiments (e.g., device 1100, having similar elements as described for FIGS. 1A-D, FIGS. 2A-D, and FIGS. 3A-E above) the testing device can incorporate rolling wheels 1110a-b and 1120 a-b that have a tacky or sticky surface, which provide a relatively strong but readily reversible contact with the skin surface during use. Such wheels can be in the form of elongated cylinders that each extend over about 25% or more of the length of the testing device along the major cylindrical axis. This extended contact area similarly improves contact with the skin surface during use, and can be adapted to employ the calming features described above (e.g., textures, temperature, etc). Similarly as described above, in preferred embodiments the distance between each wheel (e.g., distance between closest edges, furthest edges, center of mass, etc of each wheel, for example between 1110a and 1110b, between 1110a and 1120a, between 1110a and 1120b, each combination of 1110a-b and 1120a-b, etc) of the device is known and recorded, for example in a computer memory of the device 1100, in a computer memory of the mobile device 1130.

As shown in FIGS. 11A-E, some embodiments (e.g., device 1100) can include handgrips 1140a-b (or more) positioned along the edge of the testing device. Handgrips 1140a-b can be configured to complement the shape of a gripping hand (for example, by being arched) and/or incorporate a friction surface in order to support simple and accurate placement during use.

Device 1100 further includes printed circuit board 1150, which includes circuitry required to communicate with and record data from encoders (not pictured) in wheels 1110a-b and 1120a-b, as well as relay such data to mobile device 1130 (e.g., memory, microcontroller unit, CPU, etc). In preferred embodiments, printed circuit board (PCB) 1150 further includes a motion sensor (e.g., accelerometer, inclinometer, scoliometer, etc), an LED (e.g., to provide a guide light for applying the device to a patient), or a wireless communication transmitter or receiver (e.g., Bluetooth, NFC, etc, to provide communication with mobile device 1130). The sensors integrated in such PCBs (e.g., motion sensor, etc) can complement or replace the function of a motion sensor of mobile phone 1130 used in device 1100. Such sensors (e.g., motion sensor) can serve to standardize performance of device 1100 across different models of mobile devices, which potentially use a disparate assortment of internal hardware and software with disparate performance, in an effort to improve or ensure adequate precision.

Figure 12F:
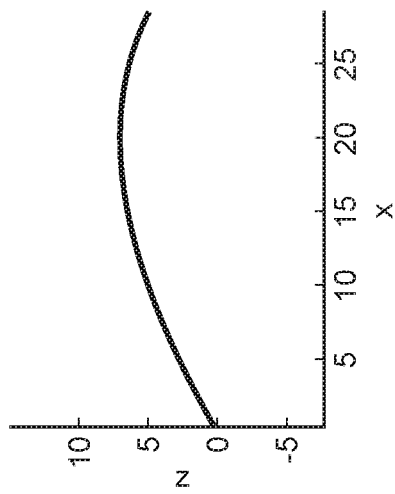
FIGS. 12F-I depict a sample three dimensional model, two dimensional top view model, two dimensional side view model, and two dimensional gluteal view model, respectively, of a patient's spine in a 90° bend position generated using data collected by a testing device of the inventive subject matter.
Figure 12H:
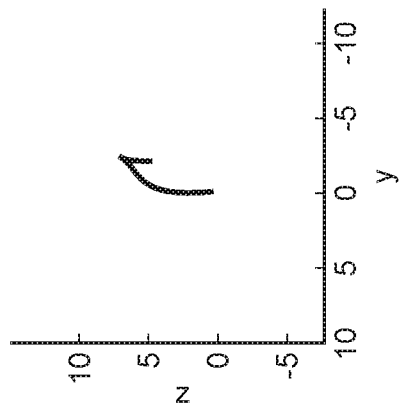
Figure 12G:
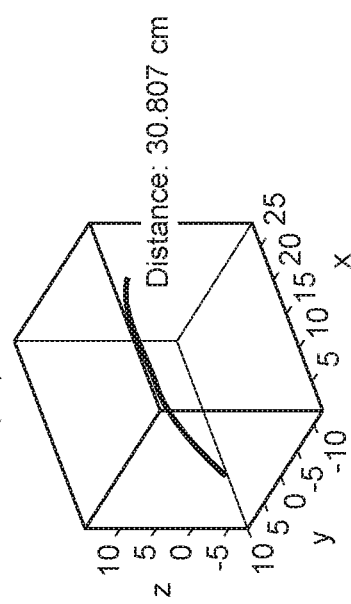
Figure 12I:
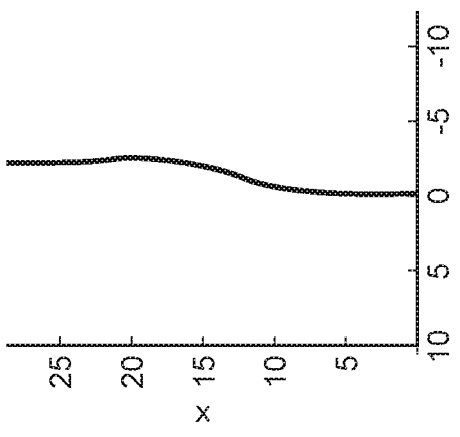

Testing or scanning of a subject can be performed with the subject in a bent-forward position (i.e. at approximately 90°) position (as shown in FIGS. 12A-C), standing straight (as shown in FIGS. 13A-B), both positions, and/or in transition between these positions (e.g., 15° bend, 30° bend, 45° bend, 60° bend, 75° bend, 105° bend, 120° bend, etc). In the example shown in FIGS. 12A-C, testing is performed in the bent-forward position. The assembled testing device 1210 is placed near the gluteal cleft of the subject (1230), with the notch of the device centered over the spine. Testing is initiated by pressing "start" on device 1210 and moving device 1210 along the spine toward the neck (directional arrow 1240) while keeping guide feature 1212 centered over the spine, and halted by pressing "stop" on device 1210.

During use of device 1210, a green indicator on the display indicates that testing should continue, whereas a red indicator on the display indicates that at least a portion of the test needs to be repeated. At the completion of the first portion of the test the subject is instructed to assume the next test position (in this instance, standing, e.g., FIGS. 13A-B, with similarly numbered elements as described for FIGS. 12A-C) and the process is repeated. When testing in the second position is complete a camera of the mobile device (e.g., 1350 of FIG. 13B) (or, alternatively, of the supporting structure, e.g., 1360) can be used to take a digital image of the subject's back while standing. In some embodiments of the inventive concept, a pair of cameras (for example, a pair of cameras provided on a mobile device or a camera of the mobile device and a camera of the supporting structure in combination) can be used to generate a three dimensional image of the subject's back. This image can be reviewed manually or subjected to image recognition software in order to provide additional data about the subject's condition. Data gathered during the testing process can be stored in a local database or transferred to an offsite database, and analysis performed (as described below) to determine of the results are normal or require further evaluation. In the event that the results are abnormal the testing device can display a prompt indicating that a visit to a medical professional (for example, an orthopedic specialist) is needed.

Figure 13C:
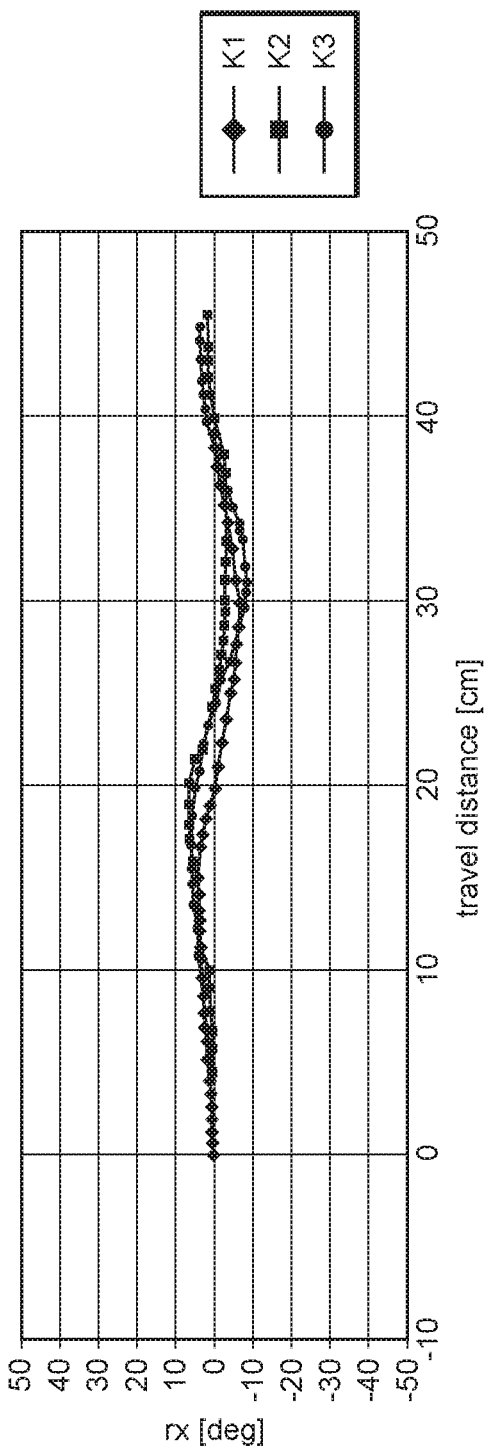
FIGS. 13C-D depict a sample plot of lateral tilt against travel distance data and a sample plot of forward tilt against travel distance data, respectively, collected from applying a testing device of the inventive subject matter to a patient in standing position.
Figure 13D:
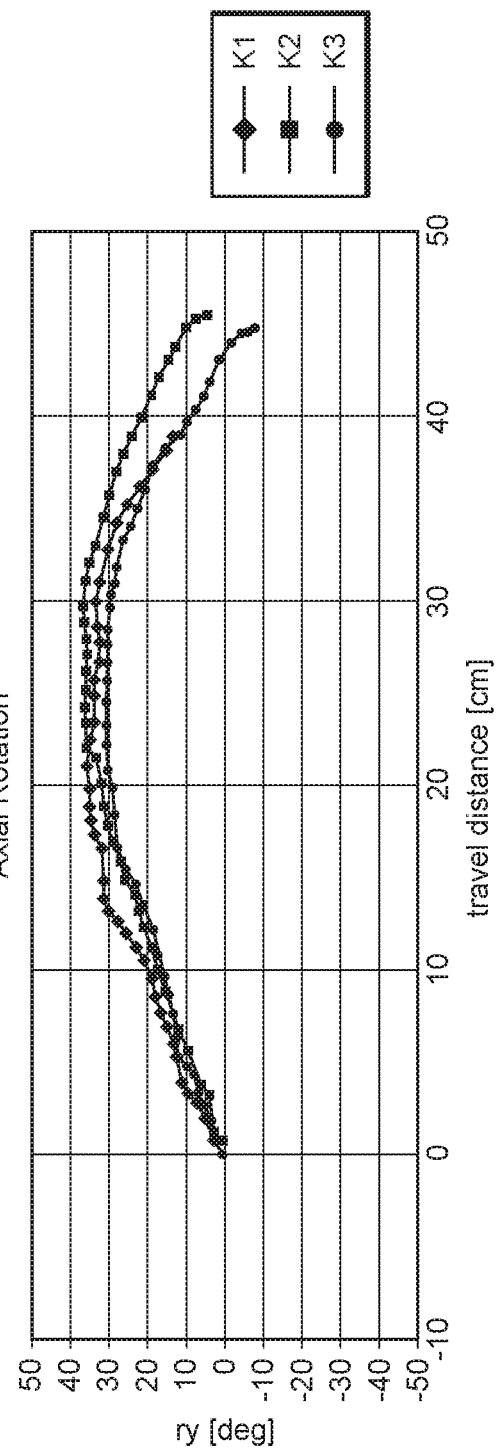
Figure 13G:
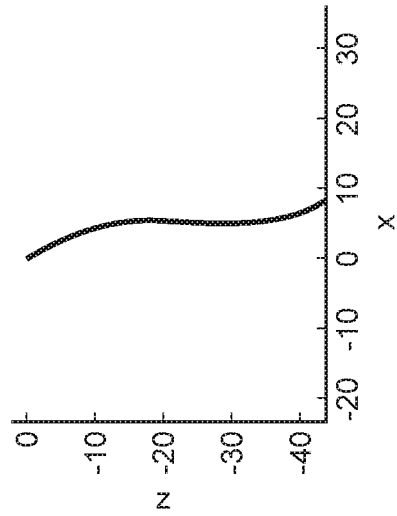
FIGS. 13E-H depict a sample three dimensional model, two dimensional top view model, two dimensional side view model, and two dimensional gluteal view model, respectively, of a patient's spine in a standing position generated using data collected by a testing device of the inventive subject matter.
Figure 13H:
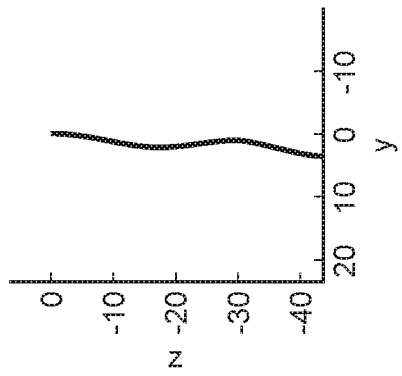
Figure 13E:
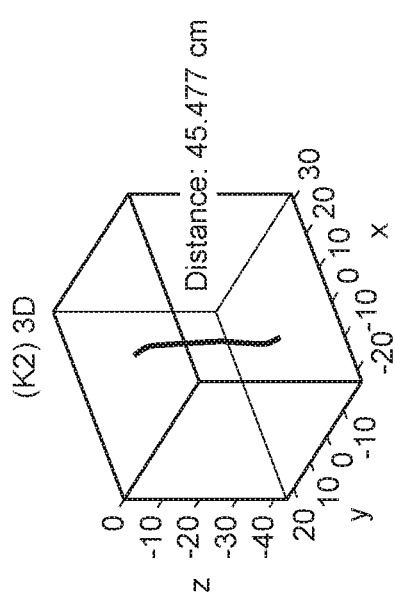
Figure 13F:
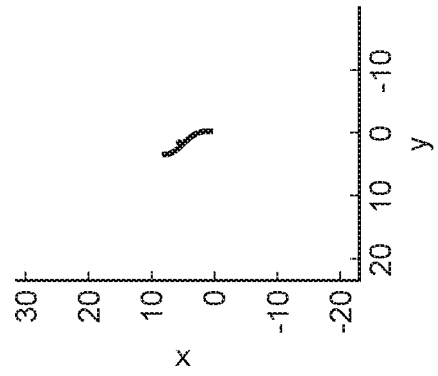

FIGS. 12D-E depict graphs of lateral tilt against travel distance and forward tilt against travel distance, respectively, based on three sets of spinal scans (S1, S2, and S3) taken using the methodology of FIGS. 12A-C. It should be appreciated that clinical parameters such as maximum vertebral rotation (e.g., lateral, forward, etc) can be extracted from the measured and processed data. In preferred embodiments, the tilt and forward angles are measured via an accelerometer on devices of the inventive subject matter (e.g., device 1210), while the spine position for each accelerometer reading is measured by the encoder(s) of the such devices. Information collected from such devices can include the duration of the test (e.g., 5.4 s), the spine length (e.g., 30 cm), maximum tilt and location (e.g., 11.4° at 38% location of the spine position. It should be appreciated that the travel distance can be presented as an absolute distance measurement (e.g., 15 cm) or a relative distance measurement (e.g., 15 cm of 30 cm=50% position along spine). Using an assumption that the lumbar region is at 0%-33% spine position, the lower thoracic region is at 33%-66% spine position, and the upper thoracic region is at 66%-100%, regional maximum tilts can also be determined (e.g., lumbar maximum 10.9°, lower thoracic 11.4°, and upper thoracic 5.5°). The approximate regions can be adjusted as required to accommodate specific dimensions of various subjects. Similar plots of data collected by the methodology of FIGS. 13A-B are depicted at FIGS. 13C-D. It should be appreciated that such measurements cannot be obtained from a subject in standing position through the use of prior art scoliometers.

FIGS. 12F-I illustrate how gyroscope and/or angular velocity data in combination with spine length and device position data gathered during a similar scan using the assembled testing device 1210 can be used to construct a three dimensional profile of the subject's spine (12F), as well as various two dimensional profiles (e.g., 12G top view, 12H side view, and 12I gluteal view). It should be appreciated that such models can be made when axial rotations along three axes are measured, and can be further improved by measuring axial rotation across six axes, nine axes, or even twelve axes, allowing additional model perspectives. Similar plots of data collected by the methodology of FIGS. 13A-B are depicted at FIGS. 13E-H.

As noted above, the Cobb angle is a commonly used clinical parameter used to diagnose scoliosis and characterize it progress and/or response to treatment. In prior art practice this figure is determined from X-ray images taken while the subject is standing. A typical prior art method for determining Cobb angle is shown in FIGS. 14A-B.

Figure 15A:
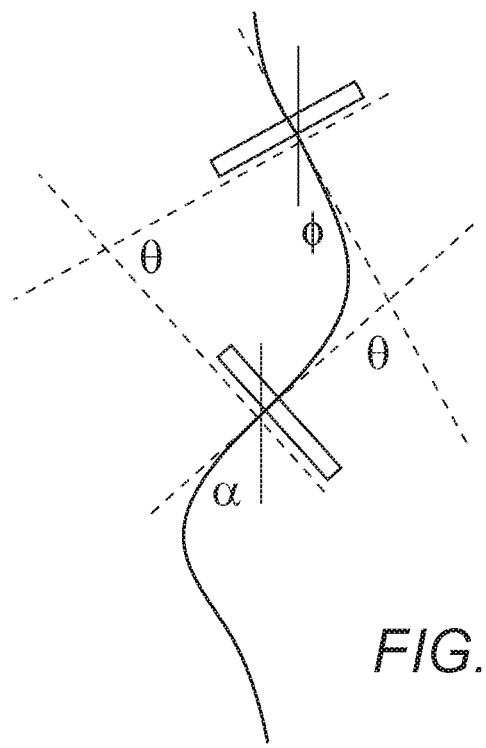
FIGS. 15A-B depict methods and results, respectively, for calculating a Cobb angle enabled by the inventive subject matter.
Figure 15B:
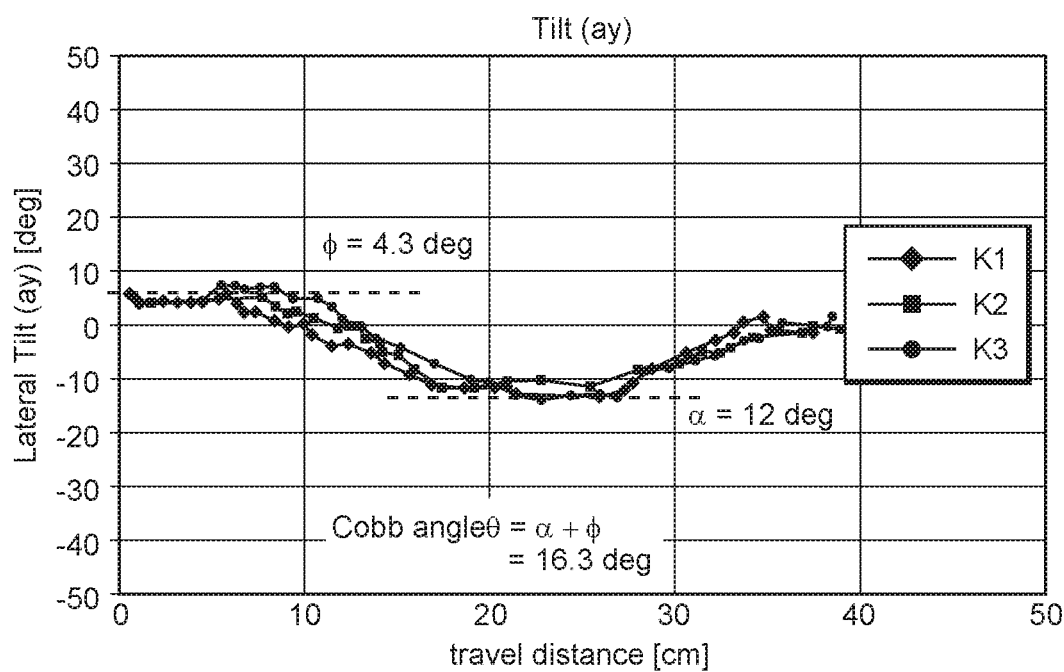

In some embodiments of the inventive concept, data obtained from an assembled testing device (e.g., FIGS. 11A-E) can be used to calculate the Cobb angle of a subject without the need for collection of an X-ray image. As shown in FIGS. 15A-B, the Cobb angle ($\theta=\phi+\alpha$) can be derived from Y-axis tilt and travel distance data (e.g., lateral tilt $\phi$ at a first spine location and lateral tilt $\alpha$ at a second spine location) gathered from the assembled testing device, for example while the subject is in a standing position. Applying such methodology to the data in FIG. 15B yields, $\phi=4.3°$ at approximately 10 cm along the spine, $\alpha=12°$ at approximately 25 cm along the spine, for a Cobb angle $\theta=16.3°$. Such data can be collected from a number of subjects and correlated with Cobb angle values derived from X-ray measurements. The results of this correlation can subsequently be applied to data provided by an assembled testing device from a specific patient to derive the Cobb angle value for that patient.

Figure 16A:
FIGS. 16A-B depict side profiles of a normal spine and a kyphosis spine.
Figure 16B:
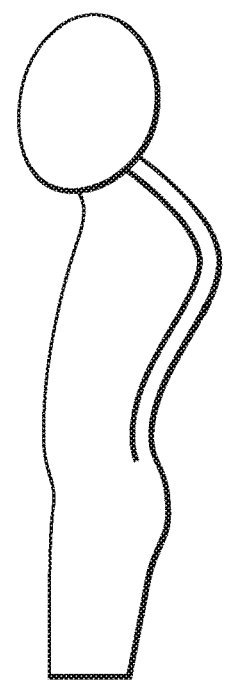
Figure 16C:
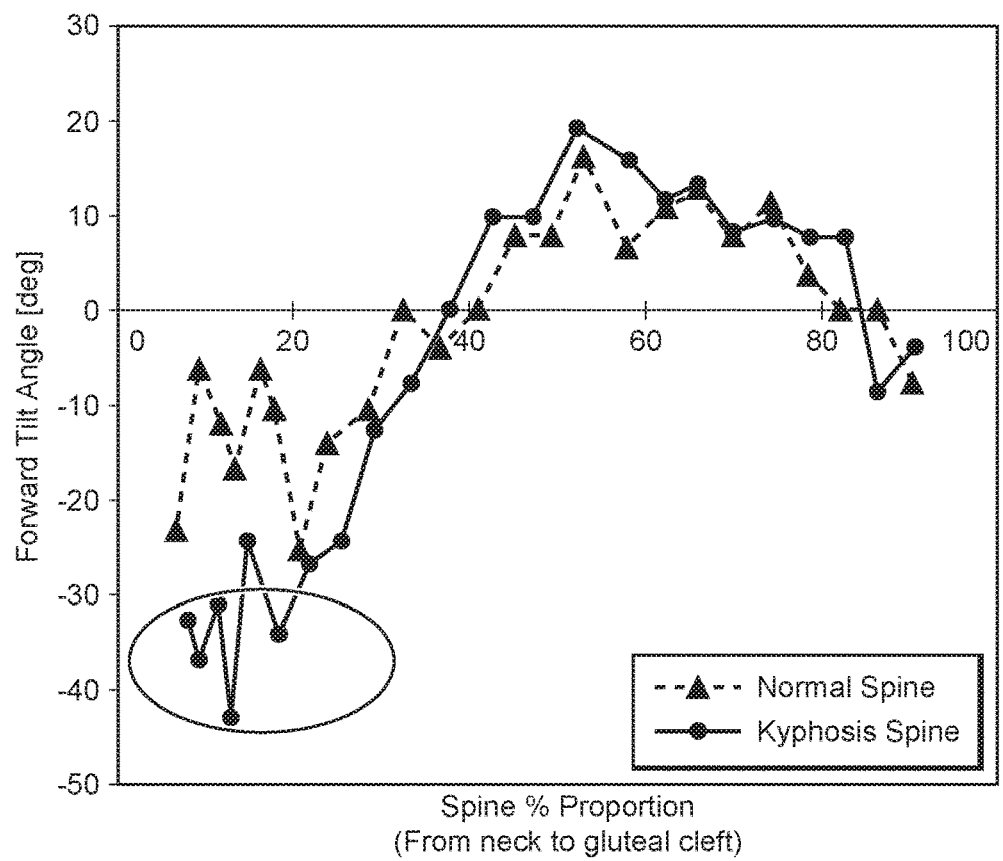
FIG. 16C depicts a sample plot of forward tilt angle against spine percent proportion generated using data collected by a testing device of the inventive subject matter.

Kyphosis, an exaggerated curve of the thoracic spine (also known as "dowager's hump," compare FIG. 16A depicting side profile of normal spine with FIG. 16B depicting side profile of kyphosis spine), can also be characterized using an assembled testing device of the inventive concept. As shown in FIG. 16C, a plot of forward tilt angle against travel distance taken from both normal individuals and individuals afflicted with kyphosis shows clear differentiation. The presence and degree of kyphosis can also be derived from three dimensional depictions of the spine derived from data provided by an assembled testing device (examples shown in FIGS. 12F-I and 13E-H). It should be appreciated that kyphosis can occur in combination with scoliosis, and that characterization using devices of the inventive concept provides data that permits diagnosis of either or both conditions from a single testing session, and without the use of X-rays.

As noted above, embodiments of the inventive concept can include software (such as programs or applications) that are configured to run on the mobile device and serve to assist a user in performance of the test and/or recording of the results. In some embodiments the software can provide a user interface that assists in performing an assessment using the assembled testing device. Such an interface can, for example, provide virtual controls for various device functions, result storage and access to stored results, modification of device setting, progress and/or status of an examination performed by the device, and/or summaries of scan results. It is contemplated that mobile applications of the inventive subject matter can be installed on mobile devices (e.g., smartphone), for example by installing the applications from a third party source (e.g., iPhone Appstore, Google Play, etc) or as a direct install from supporting structures of the inventive subject matter.

Figure 17A:
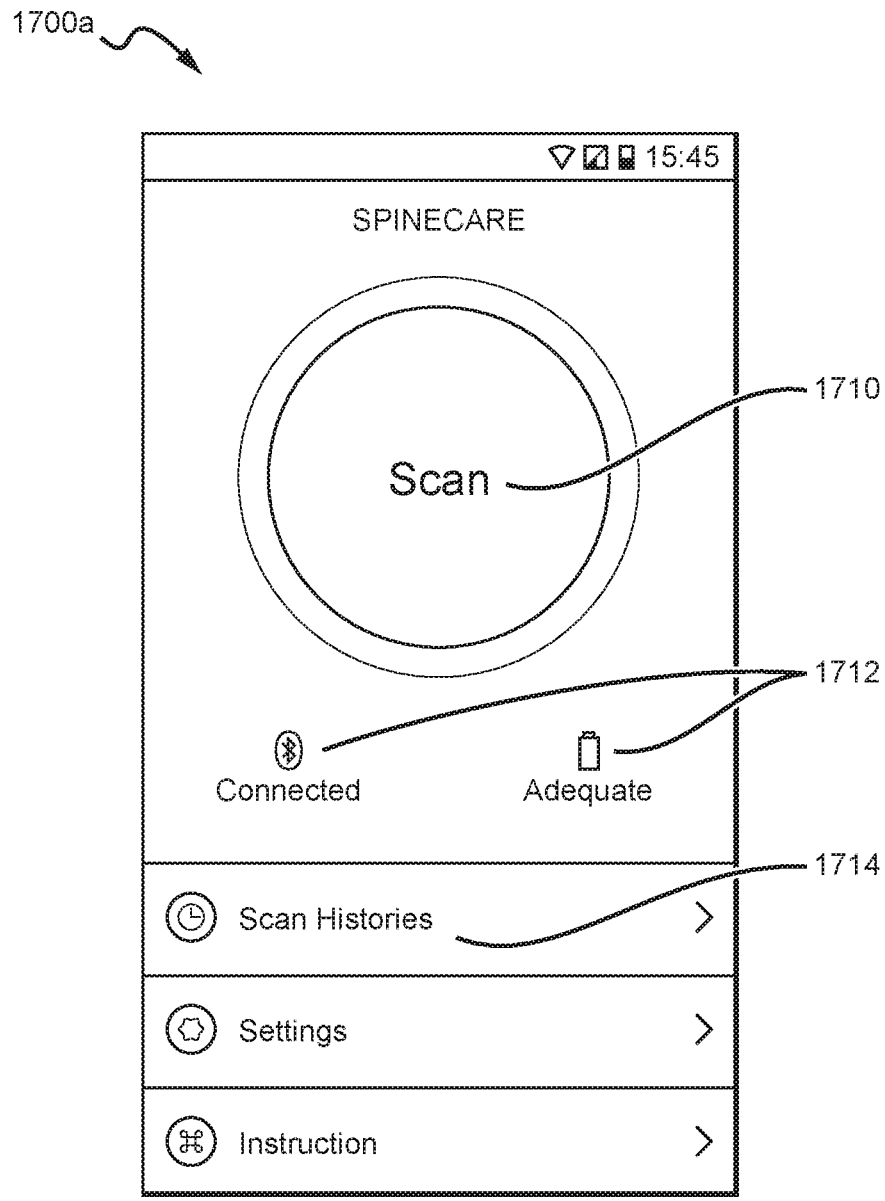
FIGS. 17A-C depict sample screen shots of a pre-scan state, a scanning state, and a post scan state, respectively, of a mobile device application of the inventive subject matter.
Figure 17B:
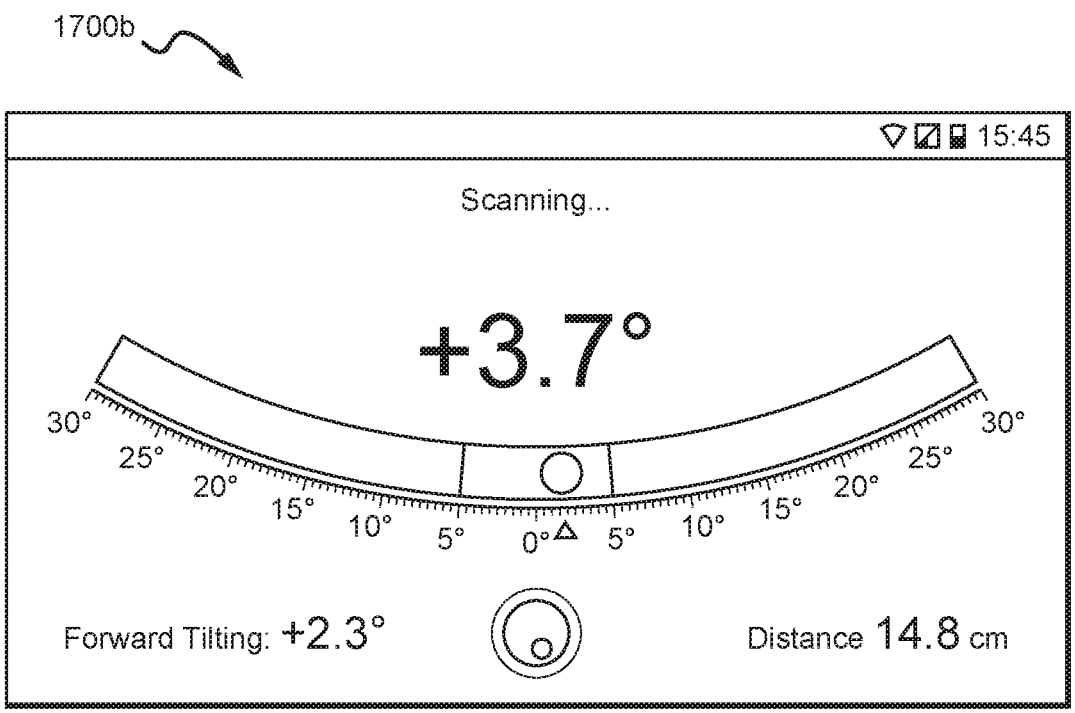
Figure 17C:
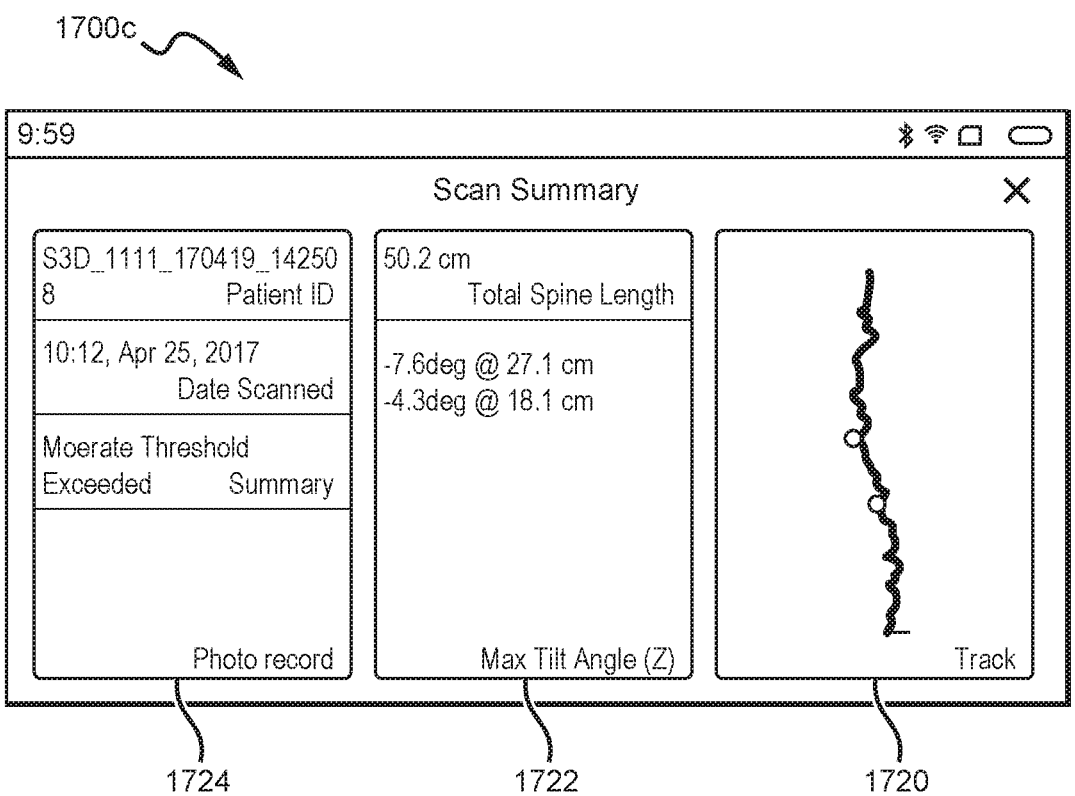

FIGS. 17A-C depict a user interface 1700 of a mobile application of the inventive subject matter installed on a mobile device in three states: pre-scan, scanning, and results (1700*a-c*, respectively). In pre-scan state 1700*a*, scan initiator 1710 can be selected by a user to make devices of the inventive subject matter ready to initiate a scan of a patient's spine. Additionally, mobile device status icons (e.g., 1712) are presented to the user signaling, for example, the mobile device has adequate battery supply to scan the patient, and that the mobile device is communicatively coupled to a supporting device (e.g., supporting structure 110) of the inventive subject matter via Bluetooth. Application menus (e.g., 1714) are also accessible, and can be selected by the user to view, for example, scan histories (e.g., stored on the device, specific to a patient, stored on a cloud server, etc), device settings (e.g., silent mode, color scheme, security settings, change user, change patient, etc), or instructions for using the device to scan the spinal column of a patient.

Scanning state 1700*b* is accessible while the device is used to scan the spinal column of a patient, and has elements largely similar to displays 700*a-b* and 800*a-b* of FIGS. 7 and 8.

Results state 1700*c* is accessible to the user once a scan is completed, or if a scan history is selected by the user. The user interface of results state 1700*c* includes map 1720, spinal features 1722, and result summary 1724. As depicted, map 1720 depicts a model of the patient's spine with anomalies indicated where detected. It is contemplated that the model can be two dimensional, three dimensional, or four dimensional, and can be manipulated (rotated, turned, selected, zoom in/out, etc) by the user. Spinal features 1722 displays relevant data from the scan of the patient's spine. For example, as depicted spinal features 1722 indicates the total length of the spine as scanned, as well as the lateral tilt angles of the spine that surpass a threshold indicative of scoliosis (e.g., 0°-5° normal, 5°-10° moderate, >10° serious, etc), along with the location of the angle along the spine (e.g., at 18.1 cm from base, at 27.1 cm from base, etc). It should be appreciated that spinal features 1722 can include as many types of feature and related information as detected for a spine (e.g., lateral tilt angle, forward tilt angle, spinal length, location along spine, etc; more than 2, 3, 5, 7, or 10 features, etc). Result summary 1724 presents summary information to the user that describes the scan. For example, result summary 1724 as depicted presents an anonymized patient identification (e.g., S3D_1111_170419_142508), the date the spinal scan was taken (e.g., hour, month, day, year, etc), as well as a conclusion reached based on analysis of the spinal scan data (e.g., moderate threshold exceeded, serious threshold exceeded, normal, etc).

Additional thresholds for lateral tilt angles to identify scoliosis can be entered by a user, or autopopulated based on data (e.g., experimental, clinical, demographic, patient specific, etc) by devices of the inventive subject matter, proprietary servers, or third-party databases. For example, normal ranges can be 0°-1°, 0°-3°, 0°-5°, 0°-7°, 0°-10°, 0°-12°, 1°-3°, 1°-5°, 1°-7°, 1°-10°, 1°-12°, 3°-5°, 3°-7°, 3°-10°, 3°-12°, 5°-7°, 5°-10°, 5°-12°, 7°-10°, 7°-12°, 10°-12°, etc. Likewise, moderate ranges can be 3°-5°, 3°-7°, 3°-10°, 3°-12°, 3°-15°, 3°-17°, 5°-7°, 5°-10°, 5°-12°, 5°-15°, 5°-17°, 7°-10°, 7°-12°, 7°-15°, 7°-17°, 10°-12°, 10°-15°, 10°-17°, 12°-15°, 12°-17°, 15°-17°, etc. Further, severe ranges can be 7°-10°, 7°-12°, 7°-15°, 7°-17°, 7°-20°, 7°-22°, 7°-25°, 10°-12°, 10°-15°, 10°-17°, 10°-20°, 10°-22°, 10°-25°, 12°-15°, 12°-17°, 12°-20°, 12°-22°, 12°-25°, 15°-17°, 15°-20°, 15°-22°, 15°-25°, 17°-20°, 17°-22°, 17°-25°, 20°-22°, 20°-25°, 22°-25°, etc.

Similarly, additional thresholds for forward tilt angles to identify kyphosis can be entered by a user, or autopopulated based on data (e.g., experimental, clinical, demographic, patient specific, etc) by devices of the inventive subject matter, proprietary servers, or third-party databases. For example, normal ranges can be 0°-11°, 0°-13°, 0°-15°, 0°-17°, 0°-20°, 0°-22°, 0°-23°, 0°-25°, 0°-27°, 0°-30°, 0°-32°, 10°-13°, 10°-15°, 10°-17°, 10°-20°, 10°-22°, 10°-23°, 10°-25°, 10°-27°, 10°-30°, 10°-32°, 13°-15°, 13°-17°, 13°-20°, 13°-22°, 13°-23°, 13°-25°, 13°-27°, 13°-30°, 13°-32°, 15°-17°, 15°-20°, 15°-22°, 15°-23°, 15°-25°, 15°-27°, 15°-30°, 15°-32°, 17°-20°, 17°-22°, 17°-23°, 17°-25°, 17°-27°, 17°-30°, 17°-32°, 20°-22°, 20°-23°, 20°-25°, 20°-27°, 20°-30°, 20°-32°, 23°-25°, 23°-27°, 23°-30°, 23°-32°, 25°-27°, 25°-30°, 25°-32°, 27°-30°, 27°-32°, 30°-32°, etc. Likewise, moderate ranges can be 10°-13°, 10°-15°, 10°-17°, 10°-20°, 10°-22°, 10°-23°, 10°-25°, 10°-27°, 10°-30°, 10°-32°, 10°-33°, 10°-35°, 10°-37°, 10°-40°, 13°-15°, 13°-17°, 13°-20°, 13°-22°, 13°-23°, 13°-25°, 13°-27°, 13°-30°, 13°-32°, 13°-33°, 13°-35°, 13°-37°, 13°-40°, 15°-17°, 15°-20°, 15°-22°, 15°-23°, 15°-25°, 15°-27°, 15°-30°, 15°-32°, 15°-33°, 15°-35°, 15°-37°, 15°-40°, 17°-20°, 17°-22°, 17°-23°, 17°-25°, 17°-27°, 17°-30°, 17°-32°, 17°-33°, 17°-35°, 17°-37°, 17°-40°, 20°-22°, 20°-23°, 20°-25°, 20°-27°, 20°-30°, 20°-32°, 23°-25°, 23°-27°, 23°-30°, 23°-32°, 20°-33°, 20°-35°, 20°-37°, 20°-40°, 25°-27°, 25°-30°, 25°-32°, 25°-33°, 25°-35°, 25°-37°, 25°-40°, 27°-30°, 27°-32°, 27°-33°, 27°-35°, 27°-37°, 27°-40°, 30°-32°, 30°-33°, 30°-35°, 30°-37°, 30°-40°, 32°-33°, 32°-35°, 32°-37°, 32°-40°, 33°-35°, 33°-37°, 33°-40°, 35°-37°, 35°-40°, 37°-40°, etc. Further, severe ranges can be 17°-20°, 17°-22°, 17°-23°, 17°-25°, 17°-27°, 17°-30°, 17°-32°, 17°-33°, 17°-35°, 17°-37°, 17°-40°, 17°-42°, 17°-43°, 17°-45°, 17°-47°, 17°-50°, 17°-52°, 17°-53°, 17°-55°, 17°-57°, 17°-60°, 20°-22°, 20°-23°, 20°-25°, 20°-27°, 20°-30°, 20°-32°, 23°-25°, 23°-27°, 23°-30°, 23°-32°, 20°-33°, 20°-35°, 20°-37°, 20°-40°, 20°-42°, 20°-43°, 20°-45°, 20°-47°, 20°-50°, 20°-52°, 20°-53°, 20°-55°, 20°-57°, 20°-60°, 25°-27°, 25°-30°, 25°-32°, 25°-33°, 25°-35°, 25°-37°, 25°-40°, 25°-42°, 25°-43°, 25°-45°, 25°-47°, 25°-50°, 25°-52°, 25°-53°, 25°-55°, 25°-57°, 25°-60°, 27°-30°, 27°-32°, 27°-33°, 27°-35°, 27°-37°, 27°-40°, 27°-42°, 27°-43°, 27°-45°, 27°-47°, 27°-50°, 27°-52°, 27°-53°, 27°-55°, 27°-57°, 27°-60°, 30°-32°, 30°-33°, 30°-35°, 30°-37°, 30°-40°, 30°-42°, 30°-43°, 30°-45°, 30°-47°, 30°-50°, 30°-52°, 30°-53°, 30°-55°, 30°-57°, 30°-60°, 32°-33°, 32°-35°, 32°-37°, 32°-40°, 32°-42°, 32°-43°, 32°-45°, 32°-47°, 32°-50°, 32°-52°, 32°-53°, 32°-55°, 32°-57°, 32°-60°, 33°-35°, 33°-37°, 33°-40°, 33°-42°, 33°-43°, 33°-45°, 33°-47°, 33°-50°, 33°-52°, 33°-53°, 33°-55°, 33°-57°, 33°-60°, 35°-37°, 35°-40°, 35°-42°, 35°-43°, 35°-45°, 35°-47°, 35°-50°, 35°-52°, 35°-53°, 35°-55°, 35°-57°, 35°-60°, 37°-40°, 37°-42°, 37°-43°, 37°-45°, 37°-47°, 37°-50°, 37°52°, 37°-53°, 37°-55°, 37°-57°, 37°-60°, 40°-42°, 40°-43°, 40°-45°, 40°-47°, 40°-50°, 40°-52°, 40°-53°, 40°-55°, 40°-57°, 40°-60°, 45°-60°, 50°-60°, 55°-60°, >60°, etc.

It should be appreciated that results state 1700c can further include additional information, such as identifying the user/operator of the device during the scan, identifying that the scan data or results are inconsistent with other scan data or results for a specific patient, or an indication that additional analysis is available or required. For example, results state 1700c can further instruct a user or a patient to seek medical attention or schedule an appointment with a medical professional (e.g., based on patient's medical insurance, selected from trusted healthcare providers, in-network providers, healthcare provider expertise, location of patient or device relative to healthcare provider, availability of healthcare provider, facilities required for treatment of patient, facilities available at healthcare provider, etc). Results state 1700c can also direct a user/patient to further comments made by a healthcare professional regarding the spine scan data, or whether the patient has completed the instructions issued by the mobile application.

It should also be appreciated that the results of scans that have diagnostic value (e.g., indicate scoliosis, kyphosis, other spinal deformity), or all scans, can be forwarded to relevant databases, for example databases maintained by healthcare providers for a particular subject, veterinary care providers, athletic organizations, academic organizations, etc. Similarly, mobile applications of the inventive subject can receive relevant subject related data from such third party databases (e.g., healthcare providers for a particular subject, veterinary care providers, athletic organizations, academic organizations, etc). It should also be appreciated that mobile applications of the inventive subject matter forward all collected and received data to proprietary cloud based servers, for further data analysis (e.g., big data analysis, identifying false positives, false negatives, refining algorithms for identifying spinal deformities, for identifying other spinal conditions). In such proprietary embodiments, it is contemplated such compilation of data and big data analysis can be made available to third parties as a subscription service.

In another embodiment of the inventive concept, differences in travel between the left wheel or roller and the right wheel or roller can be utilized by the testing device to evaluate images (such as photographs or radiographs) of a test subject. In such an embodiment the testing device can be centered over a portion of the image representing the spinal column and moved along its length. Lateral curvature of the spinal column represented in the image results in differential rates of movement between the left and right wheels or rollers. For example, an image displaying a spine that curves to the right would result in a left wheel or roller traveling a shorter distance than a right wheel or roller as the testing device is moved over that portion of the image. Such data can be gathered from encoders incorporated into the wheels or rollers (as described above). These differences can be used to calculate the Cobb angle typically used to characterize scoliotic deformation. In this way a testing device of the inventive concept can be used to derive clinically useful information from current and archived data when the patient is not immediately available. It should be appreciated that an application or program running on a mobile device incorporated into the assembled testing device can have a mode for testing live subjects and a separate mode for characterizing such stored data.

It should also be appreciated that use of balls (e.g., ball-in-socket) as rollers further allows the direction of the device to be mapped or recorded by the device. For example, while use of wheels requires detecting differences in speed, acceleration, and distance traveled between the wheels on the device in order to discern the movement of the device, tracking the roll of a ball allows the device to directly tell which direction the each ball (e.g., corner of the device) move at any given moment.

As noted above, many mobile devices (for example, smart phones, tablets, etc.) include sensors other than accelerometers that can be utilized in conjunction with a supporting structure to aid in assessing scoliosis and/or kyphosis. For example, magnetic field sensors can be used to aid in orientation of the testing device and/or in sensing the passage of magnetic encoders. Infrared sensors (such as proximity sensors) can be used to determine that the testing device is being utilized on an actual test subject, thereby improving the quality of the testing database by preventing the submission of falsified data. Similarly, spectral analysis of image data gathered as part of the testing procedure can be used to verify that the same subject identifier is not being utilized for multiple subjects, or that the same test subject does not appear under different identifications.

It should also be appreciated that while the devices, systems, and methods of the inventive subject matter are presumed useful to detect spinal disorders in patients (e.g., people), it is also contemplated that the inventive subject matter can be used to characterize the condition of spinal deformities in animals (e.g., vertebrates), as well as used on model or dummy devices to train provide training or instruction to health care workers. It should also be appreciated that the inventive subject matter can also be applied to detect anomalies in mechanical structures (e.g., tension in couplings, buckling, mechanical fatigue in rods, etc) or robotic limbs/appendages (e.g., robotic arm, etc). In such embodiments, it is anticipated that forward tilting, lateral tilting, and traveled path tolerances will be informed based on the mechanical properties the material or structure that is evaluated.

Although described above in terms of incorporating a mobile device, in some embodiments of the inventive concept the supporting structure can include a display that permits direct use of the supporting structure to carry out the above described analytical functions. In such embodiments the supporting structure can include an internal CPU and/or provide communications capability with an external CPU. Such an external CPU can include a CPU of a mobile device in communication with but not coupled to the supporting structure, a laptop computer, a tablet computer, a wearable computer, a desktop computer, and/or a computer at a physically separate location. Communication with such an external CPU can be provided by a wired connection (e.g. USB or Firewire cable) or a wireless connection. Suitable wireless connections and/or protocols include WiFi, Bluetooth, infrared, radio, and microwave communications. In some embodiments communication with such an external CPU can be provided over the internet, for example using a commercial ISP or wireless service provider.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for characterizing a condition of a spinal deformity in a subject, comprising:
   a testing device comprising:
   a mobile device comprising an accelerometer, a display, and a CPU; and
   a supporting structure comprising an upper portion configured to secure the mobile device, a lower portion having a first side and a second side opposed to one another and a lower surface coupled to both the first side and the second side, wherein the lower surface comprises a first roller positioned at or near the first side, a second roller positioned at or near the second side, and a notch interposed between the first roller and the second roller, and wherein at least one of the first roller and the second roller comprise an encoder;
   placing, while the subject is in a first test position, the the testing device on a first starting position along the spine of the subject, such that the notch of the testing device is centered on the spine;
   moving the testing device along the spine on the first roller;
   while moving the testing device, collecting data related to a first distance traveled from the encoder associated with the first or second roller of the testing device and at least one of
   (1) data related to a first lateral tilt from the testing device or (2) data related to a first forward tilt from the testing device;
   placing, while the subject is in a second test position, the testing device on a second starting position along the spine, such that the notch of the testing device is centered on the spine;
   moving the testing device along the spine on the first roller;
   while moving the testing device, collecting data related to a second distance traveled from the encoder associated with the first or second roller of the testing device and at least one of (1) data related to a second lateral tilt from the testing device or (2) data related to a second forward tilt from the testing device;
   providing the data related to the first and second distance traveled and at least one of (1) the first and second lateral tilt or (2) the first and second forward tilt to a database;
   comparing the data related to either of (1) the first or second lateral tilt or (2) the first or second forward tilt to a stored value to make a determination of the condition of the spinal deformity; and
   generating a report related to condition of the spinal deformity, wherein the condition is one of (1) presence of a scoliosis deformity, (2) presence of a kyphosis deformity, or (3) no scoliosis or kyphosis deformity in the subject.

2. The method of claim 1, further comprising acquiring a digital image of the back of the subject.

3. The method of claim 1, wherein presence of a scoliosis deformity is determined when either of the first or second lateral tilt exceeds 10°.

4. The method of claim 1, wherein presence of a kyphosis deformity is determined when either of the first or second forward tilt exceeds 30°.

5. The method of claim 1, wherein the report comprises a relationship between the first distance traveled and at least one of the first lateral tilt or the first forward tilt.

6. The method of claim 1, wherein the report comprises a relationship between the second distance traveled and at least one of the second lateral tilt or the second forward tilt.

7. The method of one of claim 1, wherein data related to speed or acceleration is collected from the encoder.

* * * * *